(12) United States Patent
Kaltenboeck

(10) Patent No.: US 7,252,937 B2
(45) Date of Patent: Aug. 7, 2007

(54) HIGH-SENSITIVITY REAL-TIME POLYMERASE CHAIN REACTION FOR DETECTION OF NUCLEIC ACIDS

(75) Inventor: Bernard Kaltenboeck, Auburn, AL (US)

(73) Assignee: Auburn University, Auburn, AL (US)

( * ) Notice: Subject to any disclaimer, the term of this patent is extended or adjusted under 35 U.S.C. 154(b) by 225 days.

(21) Appl. No.: 10/364,839

(22) Filed: Feb. 11, 2003

(65) Prior Publication Data

US 2003/0219788 A1 Nov. 27, 2003

Related U.S. Application Data

(60) Provisional application No. 60/356,033, filed on Feb. 11, 2002.

(51) Int. Cl.
*C12Q 1/68* (2006.01)
*C12P 19/34* (2006.01)
*C07H 21/04* (2006.01)

(52) U.S. Cl. ............ 435/6; 435/91.2; 536/24.31; 536/24.32; 536/24.33

(58) Field of Classification Search ............ 435/6, 435/91.1, 91.2; 536/24.31, 24.33, 24.32
See application file for complete search history.

(56) References Cited

U.S. PATENT DOCUMENTS

| | | | |
|---|---|---|---|
| 6,130,047 A | 10/2000 | Nadeau et al. | 435/6 |
| 6,287,765 B1 | 9/2001 | Cubicciotti | 435/6 |
| 6,406,891 B1 * | 6/2002 | Legerski | 435/91.1 |
| 6,551,778 B1 | 4/2003 | Harvey et al. | 435/6 |

OTHER PUBLICATIONS

Huang et al. Quantitative detection of *Chlamydia* spp. by fluorescent PCR in the LightCycler. Biothechniques, Vo. 30, No. 1, p. 150-157, 2001.*
Huang et al. Quantitative detection of *Chlamydia* spp. by fluorescent PCR in the LightCycler. Biothechniques, Vo. 30, No. 1, p. 150-152, 154-157, 2001.*
Schawab et al. Concentration and purification of beef extract mock elutes from water samples for the detection of Enteroviruses, Hepatitis A virus, and Norwalk virus by RT-PCR. Appl. and Environ. Microbiol., vol. 61, No. 2, pp. 531-537, 1995.*
Everett et al. The ribosomal intergenic spacer and domain I of 23S rRNA gene are phylogenetic markers for *Chlamydia* spp. International J.Systematic Bacteriol., vol. 47, No. 2, pp. 461-473, 1997.*
The Light Cycler™—The Smartest Innovation for More Efficient PCR. Biochemica 1998, No. 2, 4-7.
Apfalter et al. Multicenter Comparison Trial of DNA Extraction Methods and PCR Assays for Detection of *Chlamydia pneumoniae* in Endarterectomy Specimens. J. Clin. Microbiol. 2001, 39:519-524.
Boman et al. Molecular Diagnosis of *Chlamydia pneumoniae* infection. J. Clin. Microbiol. 1999, 37:3791-3799.
DeSilva et al. Rapid Genotyping and Quantification on the LightCycler™ with Hybridization Probes. Biochemica 1998, No. 2, 12-15.
Everett et al. The Ribosomal Intergenic Spacer and Domain I of the 23S rRNA Gene Are Phylogenetic Markers for *Chlamydia* spp. Int. J. System. Bacteriol. 1997, 47:461-473.
Everett et al. Rapid Detection of the *Chlamydiaceae* and Other Families in the Order *Chlamydiales*: Three PCR Tests. J. Clin. Microbiol. 1999, 37:575-580.
Everett et al. Identification of Nine Species of the *Chlamydiaceae* Using PCR-RFLP. Int. J. System. Bacteriol. 1999, 49:803-813.
Hecker et al. High and Low Annealing Temperatures Increase Both Specificity and Yield in Touchdown and Stepdown PCR. BioTechniques 1996, 20:478-485.
Huang, et al. Quantitative Detection of *Chlamydia* spp. by Fluorescent PCR in the LightCycler. 2001, 30:150-157.
Johnson et al. Evaluation of Nucleic Acid Amplification Tests as Reference Tests for *Chlamydia trachomatis* Infections in Asymptomatic Men. J. Clin. Microbiol. 2000, 38:4382-4386.
Smieja et al. Replicate PCR Testing and Probit Analysis for Detection and Quantitation of *Chlamydia pneumoniae* in Clinical Specimens. J. Clin. Microbiol. 2001, 39:1796-1801.
"High Pure PCR Template Preparation Kit," Dec. 12, 2006, pp. 15-24 <http://www.roche-applied-science.com/prod_man/pdf/chapter2/page_15-24.pdf>.
DeGraves et al., "High-Sensitivity Quantitative PCR Platform," *Bio Techniques* 34:106-115 (2003).
Don et al., "'Touchdown' PCR to Circumvent Spurious Priming During Gene Amplification," *Nucleic Acids Research*, 19:4008 (1991).
Kaltenboeck et al., "Structures of and Allelic Diversity and Relationships among the Major Outer Membrane Protein (ompA) Genes of the Four Chlamydial Species," *Journal of Bacteriology*, 175:487-502 (1993).
Kaltenboeck et al., "Two-Step Polymerase Chain Reactions and Restriction Endonuclease Analyses Detect and Differentiate ompA DNA of *Chlamydia* spp.," *Journal of Clinical Microbiology*, 30:1098-1104 (1992).

* cited by examiner

*Primary Examiner*—Suryaprabha Chunduru
(74) *Attorney, Agent, or Firm*—Clark & Elbing LLP

(57) ABSTRACT

The invention features methods that are capable of detecting single target molecules in a sample input volume of, e.g., 5 μl, and of quantifying organismal, e.g., chiamydial, DNA. Desirably, these methods employ a single tube format coupled with fluorescent detection of amplicons. This approach facilitates the application of quantitative PCR (qPCR) to microbiological diagnosis in clinical settings. The invention also features primers and probes for the detection of *Chlamydia*. The use of specific hybridization probes with qPCR amplification provides the ability for identification of individual species or strains of microorganisms.

20 Claims, 3 Drawing Sheets

HIGH-SENSITIVITY REAL-TIME POLYMERASE CHAIN REACTION FOR DETECTION OF NUCLEIC ACIDS

CROSS-REFERENCE TO RELATED APPLICATIONS

This application claims priority to U.S. Provisional Application No. 60/356,033, filed Feb. 11, 2002, hereby incorporated by reference.

STATEMENT REGARDING FEDERALLY SPONSORED RESEARCH

This work was supported in part by the Government under Grant No. AI-38977 from the National Institute for Allergy and Infectious Disease. The Government has certain rights in this invention

BACKGROUND OF THE INVENTION

The invention relates to the fields of detection and amplification of nucleic acids.

The diagnostic use of polymerase chain reaction (PCR) in clinical microbiology has vastly increased our understanding of infection by *Chlamydia* bacteria (Boman, J. et al. J. Clin. Microbiol. 1999, 37:3791-3799; Johnson, R. et al., J. Clin. Microbiol. 2000, 38:4382-4386). However, several factors impede optimal diagnostic use of the high sensitivity of this method. In particular, all sensitive and specific assays for application to diagnostic microbiology require post-PCR processing by highly skilled personnel. This requirement is particularly true of nested PCR methods that are exceedingly sensitive to cross-contamination by product carryover. In addition, the preservation of nucleic acid targets in specimens is often poor, and the methods of DNA or nucleic acid extraction are inadequate for retrieval of target DNA at low concentration (Apfalter, P. et al. J. Clin. Microbiol. 2001, 39:519-524). Finally, specimens with low amounts of microorganisms, e.g., chlamydiae, have a Poisson distributed sampling variability, so that some aliquots from such specimens result in positive amplification while others remain negative (Smieja, M. et al. J. Clin. Microbiol 2001, 39:1796-1801).

The amount of original specimen analyzed by a single PCR may frequently be the sensitivity-limiting factor. One method for overcoming this limitation is amplifying numerous aliquots of the DNA sample (Smieja, M. et al. J. Clin. Microbiol 2001, 39:1796-1801); however, use of a single PCR reaction is desirable. Quantitative fluorescent real-time PCR methods hold the potential to detect low amounts of DNA in a single sample but have not yet been combined with nucleic acid isolation to result in high-sensitivity, high-throughput platforms suitable for wide use in clinical microbiology. Thus, there is a need for methods for highly sensitive detection of DNA.

SUMMARY OF THE INVENTION

The invention features methods, primers, and probes for detecting a microorganism, e.g., a bacterium, in a sample. The methods employ amplification of nucleic acids and address amplification in the context of low amounts of target nucleic acids, sample stability, efficient extraction of nucleic acids, optimum amplification procedures, and the choice of amplification target.

Accordingly, in a first aspect, the invention features a method of determining an amount of a target nucleic acid in a sample. In a related aspect, the invention features a method of diagnosing a microbial infection in a mammal, e.g., a human, by the detection of a target nucleic acid in a sample. The methods of these two aspects include contacting a concentrated nucleic acid sample with oligonucleotide primers capable of amplifying the target nucleic acid under appropriate conditions, a first probe labeled with a donor fluorophore, and a second probe labeled with an acceptor fluorophore to produce an amplification sample. In these methods, the first and second probes hybridize proximally to one another on the target nucleic acid, and energy from the donor fluorophore induces fluorescence from the acceptor fluorophore. The methods further include performing an amplification on the amplification sample to produce an amplification product. This amplification includes a series of step-down cycles and a series of fluorescence acquisition cycles, in each of which fluorescence from the acceptor fluorophore is detected. In the first aspect, the kinetics of an intensity of fluorescence from the acceptor fluorophore is indicative of the amount of the target nucleic acid in the sample, and in the second aspect, fluorescence from the acceptor fluorophore is indicative of the infection, while the absence of fluorescence from the acceptor fluorophore is indicative of an absence of the infection.

In one embodiment, an aliquot of a sample is contacted with a solid support, to which nucleic acid in the aliquot binds, and the nucleic acid bound to the solid support is eluted with at least two sequential volumes of 5-25 µl to produce the concentrated nucleic acid sample. Alternatively, the nucleic acid bound to the solid support is eluted, and the volume of eluate is reduced by centrifugal ultrafiltration to concentrate the nucleic acid sample. In another alternative, a plurality of aliquots of the sample may be contacted with a plurality of solid supports, to which nucleic acid binds, the nucleic acid bound to the solid supports is then eluted, and the combined volume is reduced by centrifugal ultrafiltration. The methods may also include providing a biological sample and preparing that sample for nucleic acid extraction.

In any of the foregoing methods, the solid support may include glass fiber fleece, and amplification may occur in a glass capillary. The series of step-down cycles may include, for example, six cycles having a first annealing temperature of the melting temperature of the primers, nine cycles having a second annealing temperature of 2° C. lower than the first annealing temperature, and three cycles having a third annealing temperature of 4° C. lower than the first annealing temperature. The series of fluorescence acquisition cycles may include six or more cycles having an annealing temperature lower than the melting temperature of the probes. In each acquisition cycle, fluorescence detection of the acceptor fluorophore occurs under conditions in which the first and second probes hybridize to the target nucleic acid. In one embodiment, the donor fluorophore is fluorescein or carboxyfluorescein, and the acceptor fluorophore is BODIPY® 630/650, Cy5.5, LIGHTCYCLER® Red-640 or LIGHTCYCLER® Red-705. If desired, the concentrated nucleic acid sample may be contacted with reverse transcriptase, before amplification, under conditions appropriate to reverse transcribe any RNA in the concentrated nucleic acid sample. Desirably, the reverse transcriptase is stable at ≦65° C., e.g., 70° C., 75° C., or 80° C. (e.g., THERMOSCRIPT™ RT). In one embodiment, prior to reverse transcription, the nucleic acid sample is incubated at between 65° C. and 80° C., e.g., 75° C., for 1-10 seconds, preferably 5 seconds.

Preferably, the target nucleic acid is present in a single genome in two or more copies; the target nucleic acid is DNA from *Chlamydia*; and the DNA from *Chlamydia* comprises a 23S rRNA gene. The primers may be genus-specific, and one of the first or second probes may be genus-specific, while the other probe is species- or strain-specific. The above-described methods may also employ multichannel (e.g., 530 nm, 640 nm, and 710 nm) fluorescence detection and acceptor fluorophores that are detectable only in one channel, e.g., in order to simultaneously detect or quantify nucleic acid from two or more genes or microorganisms.

The invention also provides a primer having a nucleic acid sequence of 5'-GGGGTTGTAGGGTYGAGRAIAWR-RGATC-3' (SEQ ID NO: 6); 5'-GAGAGTGGTCTCCCCA-GATTCARACTA-3' (SEQ ID NO: 7); 5'-TGACTAGGT-TGRGCAAGYRTYT-3' (SEQ ID NO: 13); or 5'-AAAGACAIATAYTCTTAAACGTCTATTATTAT-3' (SEQ ID NO: 14), where I is inosine; K is G or T; M is C or A; R is G or A; W is A or T; and Y is C or T.

In another aspect, the invention provides a probe having a nucleic acid sequence of 5'-AACGTTKARTTCT-TGAACGCGAGGTTT-3' (SEQ ID NO: 5); 5'-GRAYGA-HACAGGGTGATAGTCCCGTA-3' (SEQ ID NO: 9); 5'-ACGAAARAACAARAGACKCTAWTCGAT-3' (SEQ ID NO: 10); 5'-ACGAAAAAACAAAAGACGCTAATC-GAT-3' (SEQ ID NO: 11); 5'-ACGAAAGGAGAKMAA-GACYGACCTCAAC-3' (SEQ ID NO: 12); or 5'-CG-TAAACTAAATGTTTTGGAAACAA-3' (SEQ ID NO: 16), where H is A or C or T; I is inosine; K is G or T; M is C or A; R is G or A; W is A or T; and Y is C or T. The probe may also include a donor fluorophore conjugated to the 3' end of the probe. Alternatively, SEQ ID NOs: 10-12 may be conjugated to an acceptor fluorophore at the 5' end and a phosphate group at the 3' end.

Additionally, the invention provides a probe having a nucleic acid sequence of 5'-CCTGAGTAGRRCTAGA-CACGTGAAAC-3' (SEQ ID NO: 8) or 5'-CTTAACAAIR-CAAAWGAAATAGAAT-3' (SEQ ID NO: 15), where I is inosine; R is G or A; and W is A or T. Preferably, the probe includes an acceptor fluorophore conjugated to the 5' end of the probe and a 3' phosphate group.

By "primer" is meant an oligonucleotide that binds to a specific sequence of nucleic acid and can be elongated by a polymerase under appropriate conditions. A set of two primers is used to amplify the sequence of DNA flanked by the primers. By "probe" is meant an oligonucleotide that binds to a specific sequence of amplified nucleic acid. Typically, a probe of the invention binds to the interior, i.e., not proximal to the 3' or 5' end, of a nucleic acid sequence. A probe may contain a detectable label, e.g., a fluorophore, at the 3' or 5' end and typically cannot be extended by a polymerase. Primers and probes may also be general or genus-, species-, or strain-specific. A primer or probe may contain commonly occurring bases adenine, cytosine, guanine, thymine, or uracil, and modified bases, such as inosine.

By a "genus-specific," "species-specific," or "strain-specific" primer or probe is meant a primer or probe that binds to a sequence of DNA present in or derived from a particular genus, species, or strain of microorganism, respectively, under high stringency conditions known in the art (see, for example, Ausubel et al. *Current Protocols in Molecular Biology*, Wiley, New York 1994).

By probes that "hybridize proximally to one another" is meant two probes that hybridize to a nucleic acid sequence and are separated by 0-10 bases. Typically, the probes are separated by 1-5 bases.

By "melting temperature" or "$T_m$" is meant the temperature at which half of the concentration of a probe or primer is bound to its target DNA, when the target DNA is in excess.

By "centrifugal ultrafiltration" is meant a reduction of volume of a sample by forcing solvent, by centrifugation, through a semipermeable membrane, which does not allow a solute of interest to pass through. Typically, a membrane that passes species below a certain molecular weight is used.

By "solid support" is meant an insoluble structure suitably functionalized for binding nucleic acids. A solid support may bind nucleic acids in general or specific nucleic acid sequences.

By PCR "cycle" is meant a series of exposures of a sample to various temperatures for various times. Typically, a cycle includes annealing, elongation, and denaturation portions. The duration of each portion depends on the length and composition of the nucleic acids involved in amplification.

By a "series of step-down cycles" is meant a series of individual cycles in which the temperature of annealing is reduced after a set number of cycles. The elongation and denaturation parameters may be the same for each cycle in the series.

By a "series of fluorescence acquisition cycles" is meant a series of individual cycles in which fluorescence detection of nucleic acid occurs during each cycle.

By "microorganism" is meant an organism of microscopic size, including, without limitation, bacteria, fungi, algae, protozoa, and viruses.

The term "microbial infection" refers to the invasion of the host mammal by pathogenic microorganisms (e.g., bacteria, fungi, yeasts, viruses, protozoa). This term includes the excessive growth of microorganisms that are normally present in or on the body of a mammal. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the presence of a microbial population(s) is damaging the cells or tissues of the mammal.

Advantages of the present methods include increased stabilization, extraction, and amplification of nucleic acids and, as a result, increased sensitivity of nucleic acid detection.

Other features and advantages of the invention will be apparent from the following description of the preferred embodiments thereof, and from the claims.

DETAILED DESCRIPTION OF THE INVENTION

Figure 1:
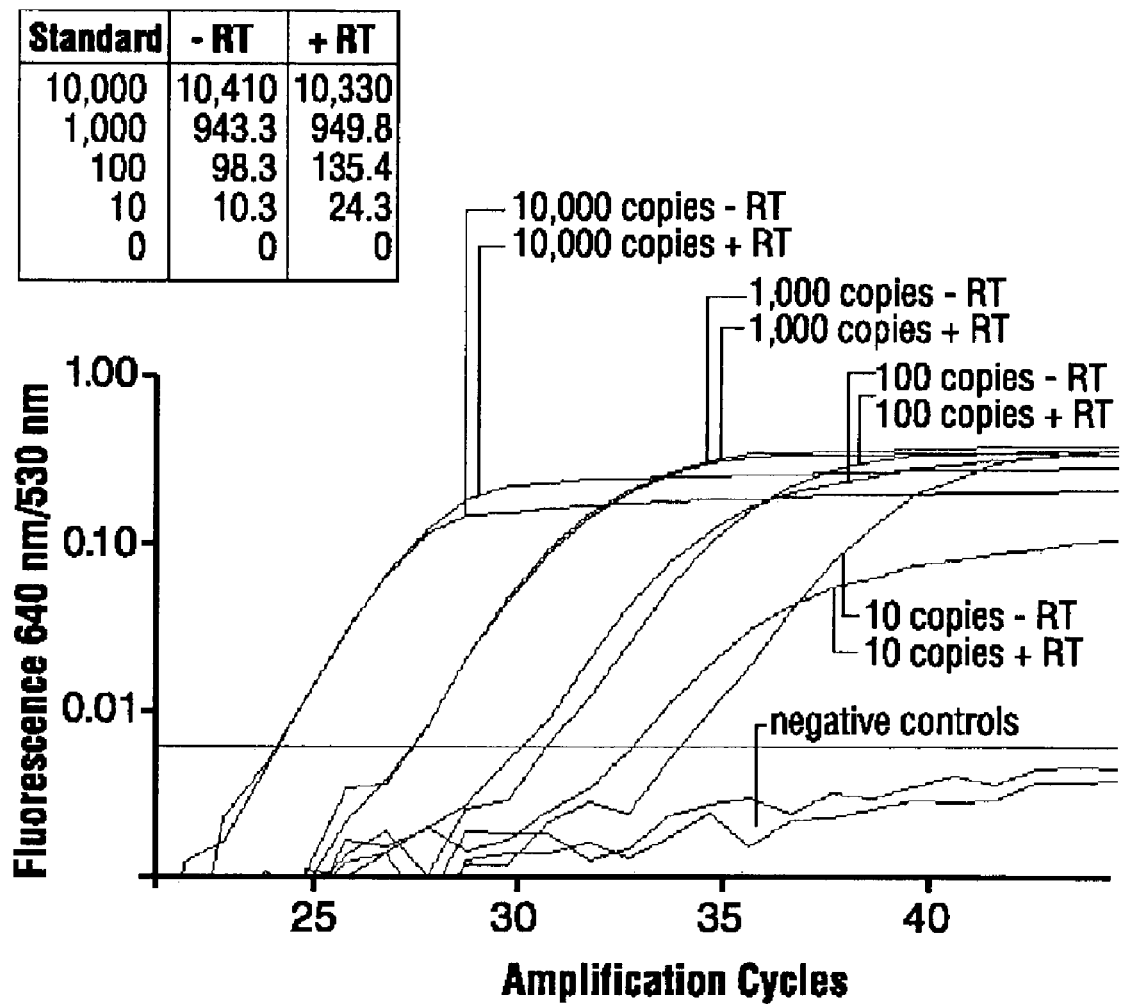
FIG. 1 is a graph showing an evaluation of the effect of one-step reverse transcription on the sensitivity of the *Chlamydia* 23S rRNA quantitative polymerase chain reaction (qPCR). *C. psittaci* B577 standards at 10,000, 1,000, 100, 10, or 0 target genomes per qPCR were amplified without (−RT) or with (+RT) one-step reverse transcription.
Figure 2:
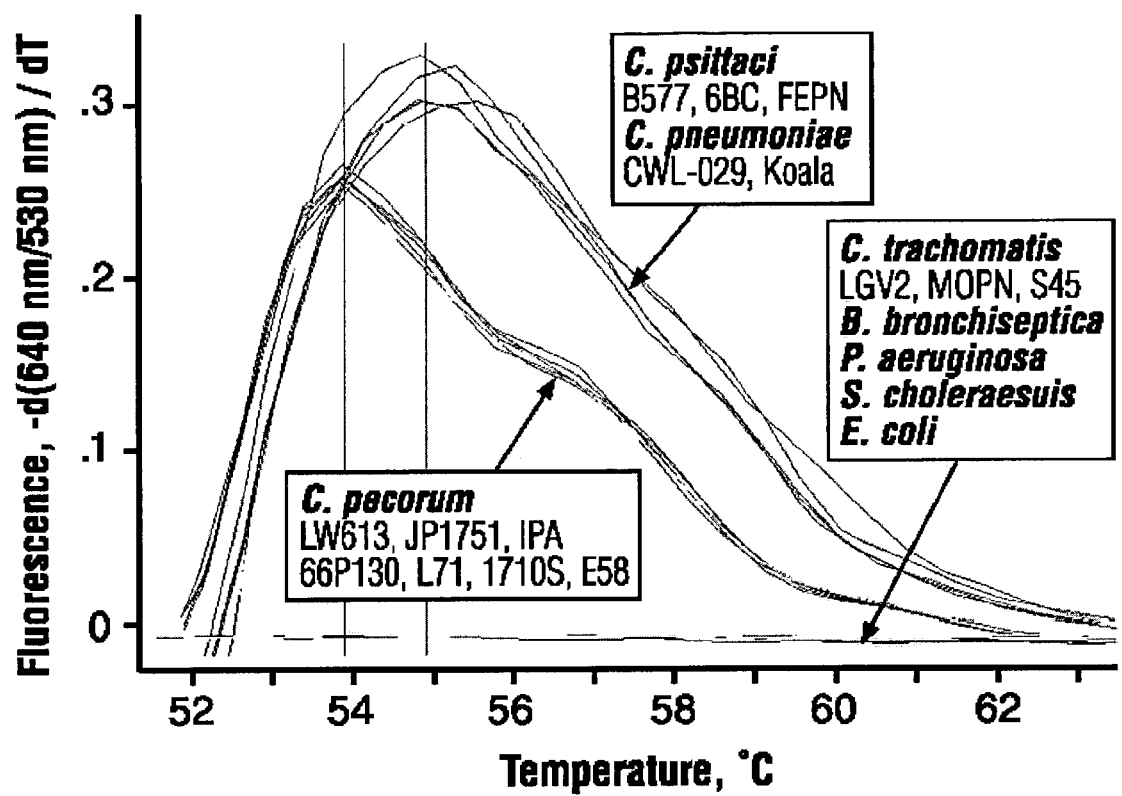
FIG. 2 is a graph showing the specificity of the *Chlamydia psittaci/pecorum/pneumoniae* 23S rRNA FRET qPCR.
Figure 3:
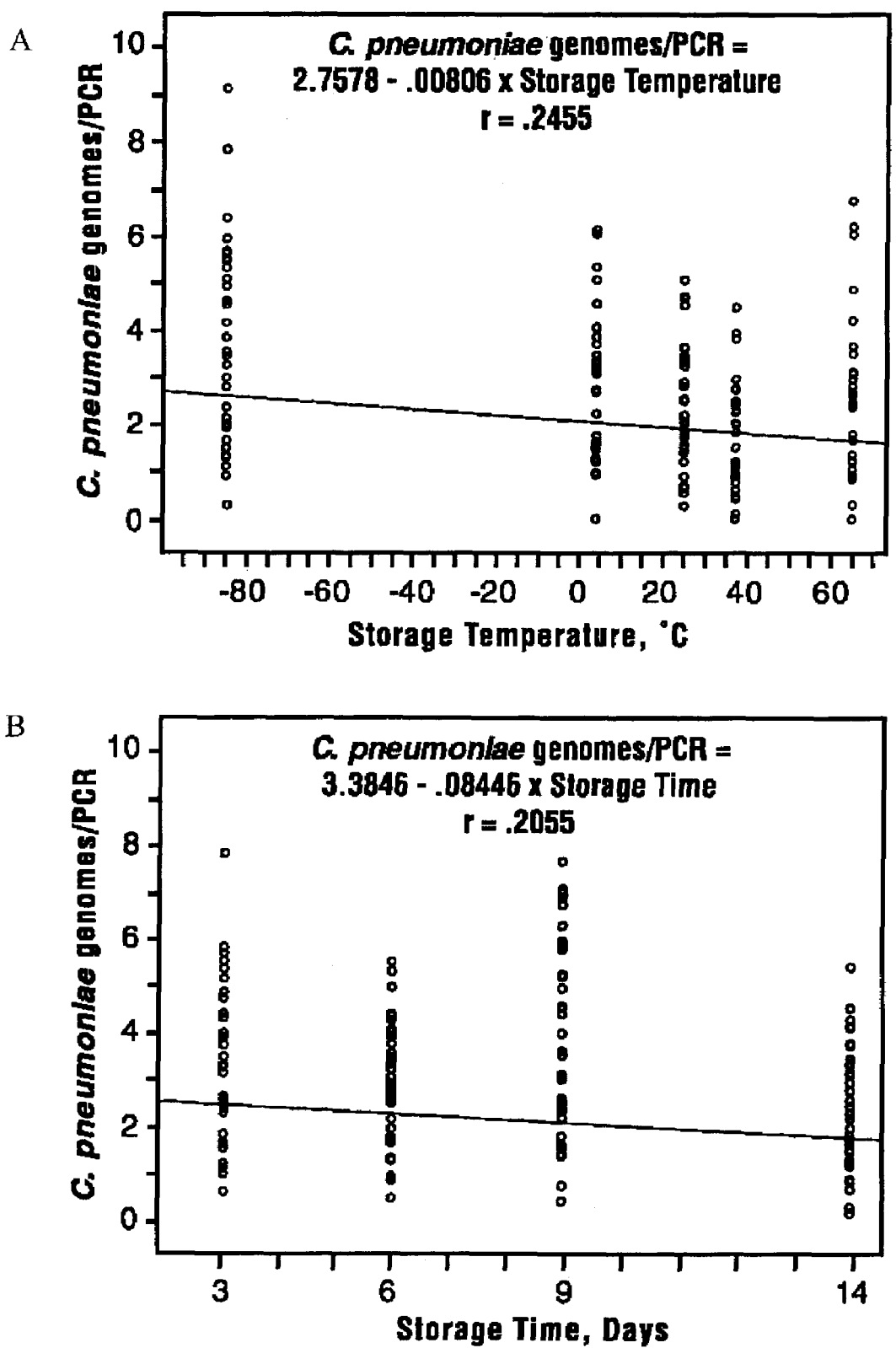
FIGS. 3A-3B are graphs showing the dependence of *C. pneumoniae* DNA recovery on temperature (3A) and time of storage of a stabilized milk sample (3B).

We have discovered methods based on PCR that are capable of detecting single target molecules in a sample input volume of, e.g., 5 μl, and of quantifying organismal, e.g., chlamydial, DNA with high accuracy. In one embodiment, these methods employ a single tube format coupled with real-time fluorescent detection of amplicons, which dramatically reduces the labor required as well as any potential for cross contamination of specimens by product carryover. This approach facilitates the application of quantitative PCR (qPCR), e.g., to microbiological diagnosis in clinical settings. Furthermore, the use of specific hybridization probes with qPCR amplification provides the ability for identification of individual species or strains of microorganisms. These methods are therefore ideally suited for diagnostics and large-scale epidemiological studies.

The methods are based on the recognition that many factors influence the sensitivity of detection by PCR. These factors include, e.g., sample preparation and stability, choice of target sequence, primers, and probes, and amplification conditions.

Sample Preparation

Stabilization. To achieve optimum PCR sensitivity for detection of DNA, e.g., chlamydial DNA, preservation of DNA is critically important, similar to the importance of RNA preservation for optimum performance of RT-PCRs (Smith, B. et al. Lancet 1991, 338:1227-1229). For example, in qPCR experiments with clinical specimens and *C. psittaci* infected mouse lungs, sample homogenization in cell culture media and/or freeze-thaw cycles of samples led to a rapid loss of chlamydial target DNA as detected by *Chlamydia* omp1-FRET qPCR (see below). In this particular example, when specimens were examined in parallel by DNA extraction before and after cryostorage, those specimens that contained low target numbers prior to freezing typically became negative after cryostorage.

Use of guanidinium buffers successfully preserves the integrity of even low amounts of target nucleic acids and allows for a simple and robust format of sample collection that tolerates lengthy storage or shipment at ambient temperature. Examples of guanidinium buffers include HIGH PURE® Binding Buffer (6 M guanidine-HCl, 10 mM urea, 20% (v/v) Triton X-100, 10 mM Tris-HCl, pH 4.4) (Roche Diagnostics Corporation, Indianapolis, Ind.) and RNA/DNA stabilization reagent for blood/bone marrow (3.3 M guanidinium isothiocyanate, Triton X-100, and mercaptoethanol, pH 6.0.) (Roche Diagnostics Corporation) (Chirgwin, J. et al. Biochemistry 1979, 18:5294-5299).

Preferably, a stabilized sample contains a final concentration of approximately 2.5-3.5 M guanidinium, and more preferably, the stabilized sample contains 2.7-3.0 M guanidinium. The use of guanidinium buffers appears to be equally well suited for detection of viral nucleic acids. Use of a concentrated buffer, e.g., HIGH PURE® Binding Buffer (6 M), is advantageous for preservation of dilute fluid specimens such as urine, serum, or milk, since concentrated buffer minimizes the dilution of nucleic acids in a sample.

Mechanical disruption. Mechanical disruption of protective cell walls might further increase the spectrum of detectable organisms to include gram-negative bacteria, microorganisms such as *Mycobacterium tuberculosis*, fungi (e.g., yeasts), parasites, and intracellular microorganisms, e.g., those within plant cells. The presence of a protective cell wall prevents the release of the nucleic acids of microorganisms, and thus prevents their sensitive detection by nucleic acid amplification techniques, such as those described herein.

One method of disruption such membranes is based on the use of inert, high-density zirconia/silica beads (for example, Cat. Nos. 11079101z, 11079105z, and 11079110z, Biospec Products, Inc., Bartlesville, Okla.) of 0.1-1 mm diameter. Such beads (0.1-1 g) are added, for example, to 400 μl of a guanidinium-based sample collection and preservation buffer. Horizontal shaking of the sample collection tube prior to nucleic acid extraction breaks up rigid membranes of organisms listed above. Simultaneously, the nucleic acids are preserved in the guanidinium buffer and can be retrieved in a nucleic acid extraction step.

Concentration. A principal limitation for the sensitivity of any qPCR is that despite a very high number of targets (e.g., 70,000) per ml original sample, the theoretically detectable number of genomes per qPCR input (e.g., 5 μl) is low (only 35 in this example). To overcome this limitation, it is necessary either i) to concentrate nucleic acids extracted from a large sample into a small volume; ii) to enrich specifically for target nucleic acids; or iii) to use a combination of both methods. New methods for concentrated extraction may be developed, or commercially available kits, e.g., the HIGH PURE® PCR Template Preparation Kit (Roche Diagnostics Corporation), may be modified to afford more concentrated samples.

One method of increasing the concentration of nucleic acid in a sample is sequentially loading several sample aliquots into a reservoir containing a solid support to which nucleic acids bind, e.g., a HIGH PURE® filter tube containing glass fiber fleece, and concentrating the elution volume, e.g., by centrifugation. Other examples of solid supports to which nucleic acids may bind include, without limitation, membranes, nucleic acid chips, beads, and resins. The parameters for centrifugation are chosen by methods known in the art and depend on the original elution volume. In one example, centrifugation is preferably for at least 10 min, more preferably 15-18 min, at 12,000×g when using a semipermeable membrane with a molecular weight cutoff of 10,000. A second method involves carefully controlled low-volume elution of nucleic acids that are bound to a solid support, e.g., glass fiber fleece. Low volume elution with two volumes of, e.g., 5-25 μl, or preferably 10-20 μl, is preferable to elution with a single, equivalent volume, e.g., 20-40 μl. The low volume eluate may then be recovered, e.g., by centrifugation at 3,000×g for 5 min. Additional steps for enrichment do not significantly increase nucleic acid recovery.

The simplicity of the extraction method, e.g., using the least number of pipetting steps possible, is important for high recovery of minimal amounts of target nucleic acids. In addition, the elution of nucleic acids at 65-75° C., preferably 72° C., is important for maximum recovery. The combined best methods for specimen preparation, nucleic acid extraction, and target nucleic acid concentration typically result in an approximately 100-μl specimen equivalent per 5-μl qPCR input. Given the reliable detection of single targets by qPCR, this results in an overall sensitivity of approximately one target copy per 100-μl original specimen volume in a single qPCR. Overall sensitivity is dependent on the total sum of the multiple qPCRs that can be assayed from a specimen (Smieja, M. et al. J. Clin. Microbiol 2001, 39:1796-1801).

qPCR

Fluorescence Resonance Energy Transfer (FRET) detection of nucleic acids employs two probes, each conjugated to a different fluorophore. One fluorophore is a donor fluorophore (e.g., fluorescein, carboxyfluorescein, or a dye with emission and excitation characteristics similar to fluorescein), which is excited by an external light source. Energy from the donor fluorophore is then transferred non-radiatively to an acceptor fluorophore (e.g., tetramethylrhodamine, BODIPY® 630/650 (6-(((4,4-difluoro-5-(2-thienyl)-4-bora-3a,4a-diaza-s-indacene-3-yl) styryloxy) acetyl)aminohexanoic acid, Cat. No. D-10000, Molecular Probes, Eugene, Oreg.), Cy5.5 (U.S. Pat. No. 5,268,486, Cat. No. 27-1799-01, Amersham Biosciences, Piscataway, N.J.), LIGHTCYCLER® Red-640 (U.S. Pat. No. 5,750,409, Cat. No. 2015161, Roche Diagnostics Corporation, Indianapolis, Ind.) or LIGHTCYCLER® Red-705 (Cat. No. 2157594, Roche Diagnostics Corporation)), if the two fluorophores are in close proximity. Typically, one probe is 3' labeled with the donor fluorophore, and the other probe is 5' labeled with the acceptor fluorophore. The two probes then hybridize to a target nucleic acid such that the fluorophores are separated, e.g., by one to five bases, in order to effect FRET.

The FRET qPCR method has several advantages over other hybridization PCR methods. Design and synthesis of the adjacent probes, each carrying only a single fluorescent label, is generally easy, and the use is robust. Moreover, the increased length of the hybridizing target sequence (compared to that of a single probe) enhances the differentiation capability of FRET qPCR in conjunction with probes of broad and narrow specificity. The present FRET qPCR platform is amenable to easy switching to other qPCR targets. To adjust between different qPCRs or different probe batches of the same qPCR, the assay chemistry (e.g., $MgCl_2$ concentration) is not changed and only critical instrument parameters, such as annealing temperature of step-down and fluorescence acquisition cycles, gains of fluorescence acquisition, and extension time at 72° C., are modified. Exemplary thermal cyclers for use with the present method include ones employing a low-volume, single-tube reaction vessel (e.g., a glass capillary), such as, LIGHTCYCLER® (Roche Diagnostics Corporation), SMART CYCLER® (Cepheid, Sunnyvale, Calif.), and ABI PRISM® (Applied Biosystems, Foster City, Calif.). Thermal cyclers that are capable of multichannel detection (e.g., 530 nm, 640 nm, and 710 nm) are desirable. In these systems, fluorescence from two or more fluorophores may be detected simultaneously, allowing for the simultaneous quantification or detection, e.g., of multiple genes or types of organism.

The present method employs several modifications to standard techniques in order to increase the sensitivity of detection. For example, step-down thermal cycling and excess of hot-start Taq polymerase (e.g., 1.5-2.0 U per 20 µl reaction) improve robustness and sensitivity of the qPCR while maintaining essentially 100% specificity. In addition, reverse transcription prior to qPCR increases the probability of detecting an organism. Targeting nucleic acid sequences present in two or more genomic copies also increases the sensitivity of detection.

RT qPCR may also be used to determine the metabolic activity of a microorganism by monitoring the level of RNA transcribed from a specific gene. This method may employ parallel qPCR (without RT) and RT qPCR. Any increase in signal in the RT qPCR compared to the qPCR would be indicative of the level of RNA transcription.

The sensitivity of PCR is limited by amplification of background DNA. To solve this problem, we have altered the thermal cycling strategy from a standard single annealing temperature approach (Huang, J. et al. BioTechniques 2001, 30:151-157) to a step-down approach (Hecker, K. et al. BioTechniques. 1996, 20:478-485) with carefully calibrated temperatures and step-down cycle numbers. The step-down process allows only low efficiency amplification during the first few cycles but ensures that primers anneal predominantly to the correct sequence. In one embodiment, thermal cycling consists of a 2 min denaturation step at 95° C. followed by 18 high-stringency step-down thermal cycles, 40 low-stringency fluorescence acquisition cycles, and melting curve determination between 50° C. and 80° C. Preferably, a series of step-down cycles includes six cycles with annealing at the calculated melting temperature ($T_m$) of the primers, followed by nine cycles with annealing at $(T_m-2)°$ C., followed by three cycles with annealing at $(T_m-4)°$ C.; elongation (e.g., at 72° C.) and denaturation (e.g., at 95° C.) may occur at the same temperatures for all step-down cycles. The $T_m$ for a primer or probe can be calculated by known methods, e.g., by using the Bostein algorithm available in software from DNASTAR® (Madison, Wis.), based on the sequences of the primer or probe and its target DNA and the salt concentration (e.g., 190 mM) of the buffer in which the nucleic acids are dissolved. Typically, the $T_m$ for a set of primers is the mean of the calculated melting temperatures of the two primers. In addition, the calculated $T_m$ is typically within 1° C. of the value measured by standard melting curve analysis. The series of step-down cycles is followed by a series of fluorescence acquisition cycles; each fluorescence acquisition cycle may employ a lower annealing temperature (e.g., 3-6° C. lower than the $T_m$ of the lower melting probe) than the final step-down cycle. In each cycle of fluorescence acquisition, FRET detection of probes may occur after annealing but before elongation. Typically, a fluorescent signal is obtained after 24 cycles (six cycles of fluorescence acquisition) for samples containing 10,000 target nucleic acids. Quantification of nucleic acids is made, e.g., by analysis of the intensity of fluorescence as a function of cycle number, by methods known in the art. When a given temperature is specified, it is understood that the actual temperature may fluctuate around that given, e.g., by ±0.50, more preferably by ±0.2° C. For example, in the first of a series of step-down cycles, the annealing temperature of a primer with a $T_m$ of 54° C. may range from 53.5-54.5° C.

Certain samples of nucleic acid, e.g., those obtained from cellular lysates with the HIGH PURE® kit, contain DNA and RNA. Contacting one of these samples with reverse transcriptase will increase the amount of target DNA (assuming the DNA is transcribed) as mRNA is reverse-transcribed into DNA. For example, reverse transcription is performed with 0.25 U SUPERSCRIPT II™ RT (U.S. Pat. Nos. 5,244,797, 5,668,005, and 6,063,608, Cat No. 18064014, Invitrogen, Carlsbad, Calif.) per qPCR for 20 min at 50° C. in a qPCR glass capillary. The use of RT increases the number of detectable targets in qPCR but can also lead to increased background that may occlude detection of small numbers of target DNA. For example, high amounts (>0.5) of SUPERSCRIPT II™ RT strongly increase the number of detectable chlamydial genomes at high copy input of nucleic acids of purified elementary bodies but render detection of low target numbers impossible because of a high background signal (see Example 7).

We have also found that use of THERMOSCRIPT™ (U.S. Pat. No. 6,063,608, Cat. No. 12236014, Invitrogen, Carlsbad, Calif.) reverse transcriptase is superior to the use of SUPERSCRIPT II™ reverse transcriptase for the production of cDNA by reverse transcription of RNA targets. The use of THERMOSCRIPT™ may improve the sensitivity of detection of *Chlamydia* or other microorganisms through amplification of RNA targets in addition to genomic DNA targets. We used THERMOSCRIPT™ reverse transcriptase at a concentration of 0.0125-0.0375 U per 20 µl reverse transcription (RT)-FRET qPCR. THERMOSCRIPT™ reverse transcriptase has a higher thermal stability than SUPERSCRIPT II™ reverse transcriptase. Taking advantage of this increased thermal stability, we added a 5 second thermal step at 75° C. prior to the initial reverse transcription step at 55° C. for 30 min in the one-step RT-FRET qPCRs. This initial 75° C. denaturation step may unfold secondary structures in RNAs and allow better access for primers. This method consistently results in higher cDNA production by the subsequent reverse transcription reaction as compared to reverse transcription performed without the initial denaturation.

Finally, targeting nucleic acids that have two or more genomic copies increases the detection sensitivity since amplification occurs at two or more sites simultaneously. For example, the chlamydial ribosomal RNA (rRNA) operon is a target that is present in two copies in the *C. trachomatis* genome (Kalman, S. et al. Nature Genetics 1999, 21:385-389; Stephens, R. et al. Science 1998, 282:754-759). Other examples of genes present in two copies in *Chlamydia* include, without limitation, mhB, groEL, oppA, oppB, oppC, dnaA, pkfA, ygdE, recA, recB, recC, trpA, and the pmp series.

The methods of the present invention can be used to assay for a variety of organisms, e.g., bacteria, fungi, eukaryotes, provided that appropriate primers and probes are available or can be synthesized using known methods. Examples of primers and probes for the detection of *Chlamydia* are listed in Table 1.

oligonucleotide primers disclosed in U.S. application Ser. No. 10/300,369, hereby incorporated by reference.

As the presence of a particular nucleic acid sequence is likely to correlate with the presence of a particular microorganism, the invention features a method for determining the presence of one or more microorganisms in a patient, e.g., a mammal. In addition, the methods of the invention can be used to evaluate the status of an individual undergoing antimicrobial therapy. In the methods of the invention, a biological sample from a patient, e.g., an individual who is suspected of having a chlamydial infection or a disease associated with a chlamydial infection, is used. For purposes of this application, a "biological sample" includes, but is not limited to, bodily secretions, bodily fluids, and tissue specimens. Examples of bodily secretions include cervical secretions, tracheal-bronchial secretions, and pharyngeal secretions. Suitable bodily fluids include, without limitation, blood, sweat, tears, cerebral spinal system fluid, serum, sputum, earwax, urine, synovial fluid, wound exudate, and saliva. Animals, cells, and tissue specimens such as from a

TABLE 1

Primers and probes for the detection of *Chlamydia*

| Primer/probe | Sequence | *Chlamydia* reactivity | QPCR target | Fluro-phore | SEQ ID NO: |
|---|---|---|---|---|---|
| 191CHOMP | 5'-GCIYTITGGGARTGYGGITGYGCIAC-3' | genus | omp/287 bp | | 1 |
| CHOMP271 | 5'-GCTCKIGACCAITKWACICCAATGTAIGG-3' | genus | | | 2 |
| CHLANPR | 5'-GAYTGIGCRTATTGGAAIKMWGCICCYAA-3' | genus | | f | 3 |
| B577PR | 5'-TACATTCAACATTTCAATTTTAGGATT-3' | a | | g | 4 |
| CPECPR | 5'-AACGTTKARTTCTTGAACGCGAGGTTT-3' | b | | g | 5 |
| CHL23SUP | 5'-GGGGTTGTAGGGTYGAGRAIAWRRGATC-3' | genus | 23 rRNA | | 6 |
| CHL23SDN | 5'-GAGAGTGGTCTCCCCAGATTCARACTA-3' | genus | 168 bp | | 7 |
| CHL23LCR | 5'-CCTGAGTAGRRCTAGACACGTGAAAC-3' | genus | | f | 8 |
| CHL23SFLU | 5'-GRAYGAHACAGGGTGATAGTCCCGTA-3' | genus | | g | 9 |
| CP23FLU | 5'-ACGAAARAACAATAGACKCTAWTCGAT-3' | b, c, d | | g | 10 |
| CP23BOD | 5'-ACGAAARAACAARAGACKCTAWTCGAT-3' | b, c, d | | h | 10 |
| CPN23FLU | 5'-ACGAAAAAACAAAAGACGCTAATCGAT-3' | d, b (weak) | | g | 11 |
| CPN23BOD | 5'-ACGAAAAAACAAAAGACGCTAATCGAT-3' | d | | h | 11 |
| CTR23FLU | 5'-ACGAAAGGAGAKMAAGACYGACCTCAAC-3' | e | | g | 12 |
| CTR23CY5 | 5'-ACGAAAGGAGAKMAAGACYGACCTCAAC-3' | e | | i | 12 |
| CHLINTUP | 5'-TGACTAGGTTGRGCAAGYRTYT-3' | genus | 16S-23S | | 13 |
| CHLINTDN | 5'-AAAGACAIATAYTCTTAAACGTCTATTATTAT-3' | genus | rRNA | | 14 |
| CHLINLCR | 5'-CTTAACAAIRCAAAWGAAATAGAAT-3' | genus | intergenic | f | 15 |
| CPSINFLU | 5'-CGTAAACTAAATGTTTTGGAAACAA-3' | c | spacer 163 bp | g | 16 | a. *C. psittaci* B577; b. *C. pecorum*; c. *C. psittaci*; d. *C. pneumoniae*; e. *C. trachomatis*; f, 5'-LIGHTCYCLER ® Red 640, 3'-phosphate; g, 3'-6-FAM; h, 5'-BODIPY ® 630/650, 3'-phosphate; i, 5'-Cy5.5, 3'-phosphate; H, A or C or T; I, inosine; K, G or T; M, C or A; R, G or A; W. A or T: Y. C or T Diagnosis The nucleotide sequences of the primers and probes used in the amplification and detection of nucleic acid determines the specificity of the method, e.g., for a particular gene and/or a particular species or strain of microorganism. The use of primers and probes that bind to the same gene for a group of different species or strains provides a tool for the detection of a microorganism, e.g., a bacterium, in that group. In some instances, the identification of the group is sufficient to determine a course of treatment. In other instances, effective treatment of a microbial infection requires information on the precise nature of the microorganism. In such instances, assays that are specific for species or strains can be used to identify the microorganism further. Table 1 shows examples of primers and probes that are specific for members of *Chlamydia*. Examples of other primers that can be used with the present method are hybrid variety of biopsies are also embraced by this term. A biological sample used in the methods of the invention may be prepared for nucleic acid extraction by methods known in the art.

In certain embodiments, the microbial infection to be detected by the invention is an infection of a bacterium selected from the group including *Chlamydia pneumoniae, C. psittaci, C. pecorum, C. abortus, C. trachomatis*, or other member of the order *Chlamydiales* (e.g., *Simkania negevensis, Parachlamydia acanthamoebae*), *Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Burkholderia cepacia, Aeromonas hydrophilia, Escherichia coli, Citrobacter freundii, Enterobacter cloacae, E. aerogenes, Klebsiella pneumoniae, K. oxytoca, Serratia marcescens, Francisella tularensis, Morganella morganii, Proteus* mirabilis, Proteus vulgaris, Providencia alcalifaciens, P. rettgeri, P. stuartii, Acinetobacter calcoaceticus, A. haemolyticus, Bordetella pertussis, B. parapertussis, B. bronchiseptica, Pasteurella multocida, P. haemolytica, Branhamella catarrhalis, Helicobacter pylori, Campylobacterfetus, C. jejuni, C. coli, Borrelia burgdorferi, V. cholerae, V. parahaemolyticus, Kingella dentrificans, K. kingae, K. oralis, Moraxella catarrhalis, M atlantae, M. lacunata, M. nonliquefaciens, M. osloensis, M. phenylpyruvica, Gardnerella vaginalis, Bacteroides fragilis, Bacteroides distasonis, Bacteroides 3452A homology group, Bacteroides vulgatus, B. ovalus, B. thetaiotaomicron, B. uniformis, B. eggerthii, B. splanchnicus, Clostridium difficile, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. matruchoti, C. mucifaciens, C. pilosum, C. propinquum, C. renale, C. riegelhi, C. sanguinis, C. singulare, C. striatum, C. sundsvallense, C. thomssenii, C. urealyticum, C. xerosis, Streptococcus pneumoniae, S. agalactiae, S. pyogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Streptococcus pneumoniae, S. agalactiae, S. pyogenes, Treponema pallidum, Burkholderia cepacia, Haemophilus actinomycetemcomitans, H. aegyptius, H. aphrophilus, H. ducreyi, H. felis, H. haemoglobinophilus, H. haemolyticus, H. influenzae, H. paragallinarum, H. parahaemolyticus, H. parainfluenzae, H. paraphrohaemolyticus, H. paraphrophilus, H. parasuis, H. piscium, H. segnis, H. somnus, H. vaginalis, Legionella adelaidensis, L. anisa, L. beliardensis, L. birminghamensis, L. bozemanii, L. brunensis, L. cherrii, L. cincinnatiensis, Legionella drozanskii L. dumoffli, L. erythra, L. fairfieldensis, L. fallonii, L. feeleii, L. geestiana, L. gormanii, L. gratiana, L. gresilensis, L. hackeliae, L. israelensis, L. jordanis, L. lansingensis, Legionella londiniensis L. longbeachae, Legionella lytica L. maceachernii, L. micdadei, L. moravica, L. nautarum, L. oakridgensis, L. parisiensis, L. pittsburghensis, L. pneumophila, L. quateirensis, L. quinlivanii, L. rowbothamii, L. rubrilucens, L. sainthelensis, L. santicrucis, L. shakespearei, L. spiritensis, L. steigerwaltii, L. taurinensis, L. tucsonensis, L. wadsworthii, L. waltersii, L. worsleiensis, Listeria denitrificans, L. grayi, L. innocua, L. ivanovii, L. monocytogenes, L. seeligeri, L. welshimeri, Mycobacterium abscessus, M. africanum, M. agri, M. aichiense, M. alvei, M. asiaticum, M, aurum, M. austroafricanum, M. avium, M. bohemicum, M. bovis, M. branderi, M. brumae, M. celatum, M. chelonae, M. chitae, M. chlorophenolicum, M. chubuense, M. confluentis, M. conspicuum, M. cookii, M. diernhoferi, M. doricum, M. duvalii, M. elephantis, M. fallax, M. farcinogenes, M. flavescens, M. fortuitum, M. frederiksbergense, M. gadium, M. gastri, M. genavense, M. gilvum, M. goodii, M. gordonae, M. haemophilum, M. hassiacum, M. heckeshornense, M. heidelbergense, M. hiberniae, M. immunogenum, M. intracellulare, M. interjectum, M. intermedium, M. kansasii, M. komossense, M. kubicae, M. lentiflavum, M. leprae, M. lepraemurium, M. luteum, M. madagascariense, M. mageritense, M. malmoense, M. marinum, M. microti, M. moriokaense, M. mucogenicum, M. murale, M. neoaurum, M. nonchromogenicum, M. novocastrense, M. obuense, M. parafortuitum, M. paratuberculosis, M. peregrinum, M. phage, M. phlei, M. porcinum, M. poriferae, M. pulveris, M. rhodesiae, M. scrofulaceum, M. senegalense, M. septicum, M. shimoidei, M. simiae, M. smegmatis, M. sphagni, M. szulgai, M. terrae, M. thermoresistibile, M. tokaiense, M. triplex, M. triviale, M. tuberculosis, M. tusciae, M. ulcerans, M. vaccae, M. wolinskyi, M. xenopi, Neisseria animalis, N. canis, N. cinerea, N. denitrificans, N. dentiae, N. elongata, N. flava, N. flavescens, N. gonorrhoeae, N. iguanae, N. lactamica, N. macacae, N. meningitides, N. mucosa, N. ovis, N. perflava, N. pharyngis var. flava, N. polysaccharea, N. sicca, N. subflava, N. weaveri, Salmonella bacteriophage, S. bongori, S. choleraesuis, S. enterica, S. enteritidis, S. paratyphi, S. typhi, S. typhimurium, S. typhimurium, S. typhimurium, S. typhimurium bacteriophage, Shigella boydii, S. dysenteriae, S. flexneri, S. sonnei, Staphylococcus arlettae, S. aureus, S. auricularis, S. bacteriophage, S. capitis, S. caprae, S. carnosus, S. caseolyticus, S. chromogenes, S. cohnii, S. delphini, S. epidermidis, S. equorum, S. felis, S. fleurettii, S. gallinarum, S. haemolyticus, S. hominis, S. hyicus, S. intermedius, S. kloosii, S. lentus, S. lugdunensis, S. lutrae, S. muscae, S. mutans, S. pasteuri, S. phage, S. piscifermentans, S. pulvereri, S. saccharolyticus, S. saprophyticus, S. schleiferi, S. sciuri, S. simulans, S. succinus, S. vitulinus, S. warneri, S. xylosus, Ureaplasma urealyticum, Yersinia aldovae, Y. bercovieri, Y. enterocolitica, Y. frederiksenii, Y. intermedia, Y. kristensenii, Y. mollaretii, Y. pestis, Y. philomiragia, Y. pseudotuberculosis, Y. rohdei, Y. ruckeri, Anaplasma bovis, A. caudatum, A. centrale, A. marginale A. ovis, A. phagocytophila, A. platys, Bartonella bacilliformis, B. clarridgeiae, B. elizabethae, B. henselae, B. henselae phage, B. quintana, B. taylorii, B. vinsonii, Borrelia afzelii, B. andersonii, B. anserina, B. bissettii, B. burgdorferi, B. crocidurae, B. garinii, B. hermsii, B. japonica, B. miyamotoi, B. parkeri, B. recurrentis, B. turdi, B. turicatae, B. valaisiana, Brucella abortus, B. melitensis, Cowdria ruminantium, Coxiella burnetii, Ehrlichia canis, E. chaffeensis, E. equi, E. ewingii, E. muris, E. phagocytophila, E. platys, E. risticii, E. ruminantium, E. sennetsu, Haemobartonella canis, H. felis, H. muris, Mycoplasma arthritidis, M. buccale, M. faucium, M. fermentans, M. genitalium, M. hominis, M. laidlawii, M. lipophilum, M. orale, M. penetrans, M. pirum, M. pneumoniae, M. salivarium, M. spermatophilum, Rickettsia australis, R. conorii, R. felis, R. helvetica, R. japonica, R. massiliae, R. montanensis, R. peacockii, R. prowazekii, R. rhipicephali, R. rickettsii, R. sibirica, and R. typhi. Accordingly, the invention discloses a method of detecting infections by the bacteria above, among others.

In other certain embodiments, the microbial infection to be detected by the invention is an infection of a fungi selected from the group including Candida aaseri, C. acidothermophilum, C. acutus, C. albicans, C. anatomiae, C. apis, C. apis var. galacta, C. atlantica, C. atmospherica, C. auringiensis, C. bertae, C. berthtae var. chiloensis, C. berthetii, C. blankii, C. boidinii, C. boleticola, C. bombi, C. bombicola, C. buinensis, C. butvri, C. cacaoi, C. cantarellii, C. cariosilignicola, C. castellii, C. castrensis, C. catenulata, C. chilensis, C. chiropterorum, C. coipomensis, C. dendronema, C. deserticola, C. diddensiae, C. diversa, C. entomaea, C. entomophila, C. ergatensis, C. ernobii, C. ethanolica, C. ethanothermophilum, C. famata, C. fluviotilis, C. fragariorum, C. fragicola, C. friedrichii, C. fructus, C. geochares, C. glabrata, C. glaebosa, C. gropengiesseri, C. guilliermondii, C. guilliermondii var. galactosa, C. guilliermondii var. soya, C. haemulonii, C. halophila/C. versatilis, C. holmii, C. humilis, C. hydrocarbofumarica, C. inconspicua, C. insectalens, C. insectamans, C. intermedia, C. javanica, C. kefyr, C. krissii, C. krusei, C. krusoides, C. lambica, C. lusitaniae, C. magnoliae, C. maltosa, C. mamillae, C. maris, C. maritima, C. melibiosica, C. melinii, C. methylica, C. milleri, C. mogii, C. molischiana, C. montana, C. multis-gemmis, C. musae, C. naeodendra, C. nemodendra, C. nitratophila, C. norvegensis, C. norvegica, C. oleophila, C. oregonensis, C. osornensis, C. paludigena, C. parapsilosis, C. pararugosa, C. periphelosum, C. petrohuensis, C. petrophilum, C. philyla, C. pignaliae, C. pintolopesii var. pintolopesii, C. pintolopesii var. sloofiae, C. pinus, C. polymorpha, C. populi, C. pseudointermedia, C. quercitrasa, C. railenensis, C. rhagii, C. rugopelliculosa, C. rugosa, C. sake, C. salmanticensis, C. savonica, C. sequanensis, C. shehatae, C. silvae, C. silvicultrix, C. solani, C. sonorensis, C. sorbophila, C. spandovensis, C. sphaerica, C. stellata, C. succiphila, C. tenuis, C. terebra, C. tropicalis, C. utilis, C. valida, C. vanderwaltii, C. vartiovaarai, C. veronae, C. vini, C. wickerhamii, C. xestobii, C. zeylanoides, and Histoplasma capsulatum. Accordingly, the invention discloses a method of detecting infections by the fungi above, among others.

In certain embodiments, the microbial infection to be detected by the invention is an infection of a protozoan selected from the group including Brachiola vesicularum, B. connori, Encephalitozoon cuniculi, E. hellem, E. intestinalis, Enterocytozoon bieneusi, Leishmania aethiopica, L. amazonensis, L. braziliensis, L. chagasi, L. donovani, L. donovani chagasi, L. donovani donovani, L. donovani infantum, L. enriettii, L. guyanensis, L. infantum, L. major, L. mexicana, L. panamensis, L. peruviana, L. pifanoi, L. tarentolae, L. tropica, Microsporidium ceylonensis, M. africanum, Nosema connori, N. ocularum, N. algerae, Plasmodium berghei, P. brasilianum, P. chabaudi, P. chabaudi adami, P. chabaudi chabaudi, P. cynomolgi, P. falciparum, P. fragile, P. gallinaceum, P. knowlesi, P. lophurae, P. malariae, P. ovale, P. reichenowi, P. simiovale, P. simium, P. vinckei petteri, P. vinckei vinckei, P. vivax, P. yoelii, P. yoelii nigeriensis, P. yoeliiyoelii, Pleistophora anguillarum, P. hippoglossoideos, P. mirandellae, P. ovariae, P. typicalis, Septata intestinalis, Toxoplasma gondii, Trachipleistophora hominis, T. anthropophthera, Vittaforma corneae, Trypanosoma avium, T. brucei, T. brucei brucei, T. brucei gambiense, T. brucei rhodesiense, T. cobitis, T. congolense, T. cruzi, T. cyclops, T. equiperdum, T. evansi, T. dionisii, T. godfreyi, T. grayi, T. lewisi, T. mega, T. microti, T. pestanai, T. rangeli, T. rotatorium, T. simiae, T. theileri, T. varani, T. vespertilionis, and T. vivax. Accordingly, the invention discloses a method of detecting infections by the protozoans above, among others.

In other certain embodiments, the microbial infection to be detected by the invention is an infection of a virus selected from the group including respiratory syncytial virus, adenovirus, influenza virus, parainfluenza virus, and rhinovirus, coxsakievirus A, herpes simplex virus, St. Louis encephalitis virus, Epstein-Barr virus, myxovirus, JC virus, coxsakievirus B, togavirus, measles virus, a hepatitis virus, paramyxovirus, echovirus, bunyavirus, cytomegalovirus, varicella-zoster virus, HIV, mumps virus, equine encephalitis virus, lymphocytic choriomeningitis virus, rabies virus, and BK virus. Accordingly, the invention discloses a method of detecting infections by the viruses above, among others.

EXAMPLES

The following examples are presented merely to illustrate various embodiments of the invention and are not meant to limit the invention in any way.

Example 1

Chlamydial Strains and Mouse Lung Infection

C. psittaci strain B577 (ATCC VR-656) and C. pneumoniae strain CDC/CWL-029 (ATCC VR-1310) were grown in BGMK cells and purified as previously described (Huang, J. et al. J. Immunol. 1999, 162:2217-2226). C. psittaci infected lung tissue was obtained from intranasally inoculated, six-week-old female BALB/c mice (Huang, J. et al. J. Immunol. 1999, 162:2217-2226). Mouse lungs were homogenized in disposable tissue grinders (Sage, Crystal Lake, Ill.) to 10% (w/v) suspensions in RNA/DNA Stabilization Reagent for Blood/Bone Marrow (Roche Diagnostics Corporation).

Example 2

Real-Time FRET qPCR

All qPCRs were performed in volumes of 15 µl reaction master mixture and 5 µl sample aliquot in glass capillaries in a LIGHTCYCLER® real-time thermal cycler (Roche Diagnostics Corporations) (Huang, J. et al. BioTechniques 2001, 30:151-157). The PCR buffer was 4.5 mM $MgCl_2$, 50 mM KCl, 20 mM Tris-HCl, pH 8.4, supplemented with 0.05% each TWEEN®-20 (polyoxyethylenesorbitan monolaurate) and NONIDET® P-40 (octylphenolpoly(ethyleneglycolether)$_n$), and 0.03% acetylated bovine serum albumin (Roche Diagnostics Corporation). Nucleotides were used at 0.2 mM (dATP, dCTP, dGTP) and 0.6 mM (dUTP). For each 20 µl total reaction volume, 1.5 U hot-start Platinum Taq DNA polymerase (Cat. No. 10966018, Invitrogen) and 0.2 U heat-labile uracil-DNA glycosylase (Roche Diagnostics Corporation) were used.

Primers and probes (Table 1) were obtained from Operon, Alameda, Calif. LIGHTCYCLER® Red-640 (LCRed640) probes were 5'-labeled and HPLC-purified; carboxyfluorescein (6-FAM) probes were 3'-labeled and used unpurified. Primers were used at 1 µM (except for the Chlamydia omp1 qPCR (Huang, J. et al. BioTechniques 2001, 30:151-157)), LCRed640 probes at 0.2 µM, and 6-FAM probes at 0.1 µM. In all qPCRs, Chlamydia genus-specific primers were combined with genus-specific LCRed640-labeled probes and with Chlamydia species- or strain-specific 6-FAM-labeled probes as listed in Table 1. For each qPCR, the reaction master mixture was freshly assembled from separate stocks of $dH_2O$, 5×PCR buffer, 5× oligonucleotides (primers and probes) in $T_{10}E_{0.1}$ buffer, 50×PCR Nucleotide Mix$^{PLUS}$ (Roche Diagnostics Corporation), Platinum Taq DNA polymerase, and uracil-DNA glycosylase.

The specific thermal protocol for the omp1 qPCR was 6×12 sec @ 60° C., 11 sec @ 72° C., 0 sec @ 95° C.; 9×12 sec @ 58° C., 11 sec @ 72° C., 95° C.; 3×12 sec @ 56° C., 11 sec @ 72° C., 0 sec @ 95° C.; 40×8 sec @ 50° C. and fluorescence acquisition, 11 sec @ 72° C., 0 sec @ 95° C. The parameters for the 23S rRNA qPCR were 6×12 sec @ 64° C., 8 sec @ 72° C., 0 sec @ 95° C.; 9×12 sec @ 62° C., 8 sec @ 72° C., 0 sec @ 95° C.; 3×12 sec @ 60° C., 8 sec @ 72° C., 0 sec @ 95° C.; 40×8 sec @ 54° C. and fluorescence acquisition, 8 sec @ 72° C., 0 sec @ 95° C. The parameters for the 16-23S rRNA intergenic spacer qPCR were 6×12 sec @ 61° C., 8 sec @ 72° C., 0 sec @ 95° C.; 9×12 sec @ 59° C., 8 sec @ 72° C., 0 sec @ 95° C.; 3×12 sec @ 57° C., 8 sec @ 72° C., 0 sec @ 95° C.; 40×8 sec @ 52° C. and fluorescence acquisition, 8 sec @ 72° C., 0 sec @ 95° C. For the 0 sec @ 95° C., the thermal cycler was ramped from 72° C. to 95° over 3-5 sec and then ramped down again. These protocols are designed for quantitative determination of 10,000 or fewer target molecules. The signal for 10,000 targets typically is distinguishable from the background after about 6 fluorescence acquisition cycles (total 24 cycles). Data were displayed and analyzed as 640 nm:530 nm fluorescence ratios.

For use as quantitative standards, C. psittaci B577 and C. pneumoniae DNA were extracted from purified elementary body preparations by the HIGH PURE® method, quantified by the PICOGREEN® DNA fluorescence assay (Cat. No. P-7589, Molecular Probes, Eugene, Oreg.), and used at 10,000, 1,000, 100, 10, and 0 genome copies per 5 µl in a background of 100 ng purified salmon sperm DNA in $T_{10}E_{0.1}$ buffer. Crude chlamydial DNAs extracted from infected yolk sac tissue (Kaltenboeck, B. et al. J. Clin. Microbiol 1992, 30:1098-1104; Kaltenboeck, B. et al. J. Clin. Microbiol 1997, 35:1835-1841) were used to analyze the specificity of detection of the *Chlamydia* 23S rRNA qPCRs.

Example 3

Stabilization of Samples

A 10% (w/v) suspension of lungs from mice infected with *C. psittaci* B577 was prepared as in Example 1, and *C. psittaci* B577 omp1 FRET qPCR analyses, as in Example 2, with DNA extracted from such samples were performed before freezing and after several freeze-thaw cycles. Within the experimental variance, the number of chlamydial targets did not decrease with cryostorage or when subjected to additional freeze-thaw cycles. In contrast, chlamydial PCR targets in DNA extracted from infected lungs that were homogenized in PBS or Tris-buffered saline were extensively degraded (50-90% reduction) if DNA extraction after homogenization was delayed by more than five minutes, or if frozen lung suspensions were thawed repeatedly.

The issue of long-term sample stability of nucleic acids was addressed in an experiment in which fresh milk was spiked with *C. pneumoniae* elementary bodies. *C. pneumoniae* was used because fresh cow milk was frequently positive for *C. psittaci* in the *Chlamydia* 23S rRNA qPCR, consistent with the high prevalence of this infection in cattle. Fresh milk was spiked with *C. pneumoniae* EB diluted to 30 genomes per ml in sucrose-phosphate-glutamate buffer (220 mM sucrose, 4 mM $KH_2PO_4$, 7 mM $K_2HPO_4$, 5 mM monosodium glutamate, pH 7.2). Six-hundred microliter aliquots were stabilized by 1:1 dilution with HIGH PURE® Binding Buffer and stored in triplicates for 3, 6, 9, or 14 days at −85° C., 4° C., 25° C., 37° C., or 65° C. DNA was extracted with the HIGH PURE® kit, eluted twice with 200 µl $T_{10}E_{0.1}$ buffer, and filter concentrated to 25 µl. Five-microliter aliquots were analyzed by *C. pneumoniae* 23S rRNA FRET qPCR (see Example 6). Data points conform to a Poisson distribution of *C. pneumoniae* genome copies detected in the qPCR aliquots, with a range of 0 to 8.6 copies at a theoretical mean of 3.6 copies per PCR. The results indicate that chlamydial nucleic acids were well preserved in the sampling approach, even under storage at high temperature for a considerable amount of time. The regression analyses in FIG. 3 reveal a ~32% linear reduction in recovery if storage temperature increases from −85° C. to 65° C., and a ~31% linear reduction in recovery if storage time increases from 3 days to 14 days. While the differences between best and worst preservation are significant (3.42 genomes at −85° C. vs. 1.76 genomes at 37° C., p=0.0002; 3.15 genomes at 3 days vs. 2.05 genomes at 14 days, p=0.0024), the recovery after 2 weeks of room temperature storage differs little from recovery after 2 weeks of −85° C. storage. Additional samples that had been stored at room temperature for several months contained chlamydial target levels similar to the 2-week level. Therefore, the guanidinium stabilization method was extremely robust under field conditions and combined facile sample collection and shipment with optimum target preservation.

Example 4

Nucleic Acid Extraction

Bovine milk, considered a difficult matrix for nucleic acid extraction, was diluted 1:10 in RNA/DNA Stabilization Reagent or 1:1 in HIGH PURE® Binding Buffer and a suspension of *C. psittaci* B577-infected mouse lung stabilized in the same reagent was added to 7,000 chlamydial genomes per ml final dilution, corresponding to 70,000 chlamydial genomes per ml original specimen. DNA was extracted by use of three commercially available kits: HIGH PURE® PCR Template Preparation Kit (Cat. No. 1796828, Roche Diagnostics Corporation); QIAAMP® Blood Kit (Cat. No. 51104, Qiagen, Valencia, Calif.); WIZARD® Genomic DNA Purification Kit (Cat. No. A1120, Promega, Madison, Wis.). These kits utilize different approaches to nucleic acid purification: nucleic acid binding in acidic chaotropic buffer to a glass fiber fleece (Vogelstein, B. et al. Proc. Natl. Acad. Sci. 1979, USA 76:615-619) followed by washing and elution at alkaline pH (HIGH PURE®); binding to a porous silica matrix in place of glass fiber (QIAAMP®); and selective precipitation of nucleic acids (WIZARD®). In all protocols, nucleic acids were eluted or dissolved in 10 mM Tris-HCl, pH 8.5, 0.1 mM EDTA ($T_{10}E_{0.1}$ buffer). Following the manufacturer's instructions, 400, 200, and 300 µl, respectively, of the spiked milk were extracted, and DNA or total nucleic acids were recovered in final volume of 400 µl (HIGH PURE®) and QIAAMP®) or 100 µl $T_{10}E_{0.1}$ buffer (WIZARD®). Extraction with the QIAAMP® and WIZARD® kits followed the manufacturers' instructions precisely. All extractions with the HIGH PURE®) kit were performed without use of the SDS/EDTA-based Tissue Lysis Buffer of the kit. Instead, 10% proteinase K solution was added directly to specimens lysed 1:10 in RNA/DNA Stabilization Reagent or 1:1 in HIGH PURE® Binding Buffer (6 M guanidine-HCl, 10 mM urea, 20% (v/v) Triton X-100, 10 mM Tris-HCl, pH 4.4). Thus, proteinase K digestion and subsequent binding of nucleic acids to the glass fiber fleece matrix of the HIGH PURE® kit was performed in both variations of the method at acidic pH and approximately 2.7 M guanidinium concentration. Duplicate 5 µl aliquots of triplicate extractions with each kit were analyzed by *Chlamydia psittaci* B577 omp1 FRET qPCR. The results in Table 2 indicate that the HIGH PURE® method is preferred when extracting low amounts of DNA.

TABLE 2

Evaluation of methods of nucleic acid extraction.

| C. psittaci B577 genomes per ml original milk sample | DNA Extraction | Sample equivalent per PCR | Theoretical Chlamydia genomes per PCR | Observed Chlamydia genomes per PCR (±SEM) | Percent recovery[a] |
|---|---|---|---|---|---|
| 70,000 | High Pure | 0.5 µl | 35 | $29.1^{\pm 3.1}$ | $83.2^{\pm 8.9}$ |
|  | QIAamp | 0.25 µl | 17.5 | $0.1^{\pm 0.2}$ | $0.3^{\pm 0.3}$ |
|  | Wizard | 1.5 µl | 105 | $1.0^{\pm 0.4}$ | $1.0^{\pm 0.4}$ |

[a] p HIGH PURE ®: QIAAMP ®, WIZARD ® = 0.000003

Example 5

Concentration of Chlamydial Target DNA

The standard HIGH PURE® method (HP, Table 3) used 400 µl of sample stabilized in RNA/DNA Stabilization Reagent (equivalent to 40 µl original milk sample) and eluted the nucleic acids in a buffer volume of 400 µl. This resulted in an original sample equivalent of 0.5 µl per 5-µl qPCR input (see Example 2). Original sample input was increased by reducing the 400-µl elution volume through centrifugal concentration. To reduce losses, the nucleic acids were eluted into centrifugal ultrafiltration devices (10,000 MW cutoff microconcentrator, Amicon, Beverly, Mass.) by inserting a HIGH PURE® sample reservoir directly into the microconcentrator. Centrifugal concentration to a 20-µl volume alleviated the problem of sample loss, while allowing for effective concentration of nucleic acids. Four consecutive 400 µl loads were added to the HIGH PURE® sample reservoir (HP conc., Table 3) to further increase the amount of nucleic acid. Duplicate 5 µl aliquots of triplicate extractions with each method were analyzed by *Chlamydia psittaci* B577 omp1 FRET qPCR. Data shown in Table 3 clearly indicate that the 4× loading and direct microconcentration approach very effectively increased the concentration of target DNA by about 60-fold at highest chlamydial loads. Results at 70 chlamydial genomes per ml of original milk sample suggest a Poisson distribution of target molecules such that some qPCR input aliquots contain one or more targets while others do not contain any target molecules. The centrifugal ultrafiltration method exhibited a high recovery at a very low theoretical chlamydial genome copy number of 2.8.

TABLE 3

| Optimization of nucleic acid extraction. | | | | | |
|---|---|---|---|---|---|
| *C. psittaci* B577 genomes per ml original milk sample | DNA extraction[a] | Sample equivalent per PCR | Theoretical *Chlamydia* genomes per PCR | Observed *Chlamydia* genomes per PCR (±SEM) | Percent recovery |
| 70,000 | HP | 0.5 µl | 35 | $19.6^{\pm 3.9}$ | $55.9^{\pm 11.3}$ |
| | HP conc. | 40 µl | 2800 | $1246^{\pm 102.8}$ | $44.5^{\pm 3.7}$ |
| | MG, 4 ml | 13.3 µl | 933 | $104^{\pm 2.5}$ | $11.1^{\pm 0.3}$ |
| | MG, 40 ml | 28.6 µl | 2000 | $65.6^{\pm 13.6}$ | $3.3^{\pm 0.7}$ |
| | MGC, 4 ml | 93.3 µl | 6533 | $46.6^{\pm 6.8}$ | $0.7^{\pm 0.1}$ |
| | MGC, 40 ml | 986 µl | 69000 | $349^{\pm 50.8}$ | $0.5^{\pm 0.1}$ |
| 7,000 | HP | 0.5 µl | 3.5 | $1.6^{\pm 0.4}$ | $46.2^{\pm 12.0}$ |
| | HP conc. | 40 µl | 280 | $83.5^{\pm 11.4}$ | $29.8^{\pm 4.1}$ |
| | MG, 4 ml | 13.3 µl | 93.3 | $9.4^{\pm 1.7}$ | $10.1^{\pm 1.9}$ |
| | MG, 40 ml | 28.6 µl | 200 | $10.2^{\pm 22}$ | $5.1^{\pm 1.1}$ |
| | MGC, 4 ml | 93.3 µl | 653.3 | $6.7^{\pm 1.0}$ | $1.0^{\pm 0.2}$ |
| | MGC, 40 ml | 986 µl | 6900 | $18.7^{\pm 1.7}$ | $0.3^{\pm 0.1}$ |
| 700 | HP | 0.5 µl | 0.35 | $0.1^{\pm 0.1}$ | $22.5^{\pm 22.5}$ |
| | HP conc. | 40 µl | 28 | $14.8^{\pm 22}$ | $52.9^{\pm 7.7}$ |
| | MG, 4 ml | 13.3 µl | 9.33 | 0 | 0 |
| | MG, 40 ml | 28.6 µl | 20 | 0 | 0 |
| | MGC, 4 ml | 93.3 µl | 65.33 | $0.3^{\pm 0.1}$ | $0.4^{\pm 0.2}$ |
| | MGC, 40 ml | 986 µl | 690 | $1.5^{\pm 0.6}$ | $0.2^{\pm 0.1}$ |
| 70 | HP | 0.5 µl | 0.035 | 0 | 0 |
| | HP conc. | 40 µl | 2.8 | $3.9^{\pm 1.0}$ | $139^{\pm 33.0}$ |
| | MG, 4 ml | 13.3 µl | 0.933 | 0 | 0 |
| | MG, 40 ml | 28.6 µl | 2 | 0 | 0 |
| | MGC, 4 ml | 93.3 µl | 6.533 | $0.23^{\pm 0.23}$ | $3.5^{\pm 3.5}$ |
| | MGC, 40 ml | 986 µl | 69 | 0 | 0 |
| 7 | HP | 0.5 µl | 0.0035 | 0 | 0 |
| | HP conc. | 40 µl | 0.28 | 0 | 0 |
| | MG, 4 ml | 13.3 µl | 0.0933 | 0 | 0 |
| | MG 40 ml | 28.6 µl | 0.2 | 0 | 0 |
| | MGC, 4 ml | 93.3 µl | 0.6533 | 0 | 0 |
| | MGC, 40 ml | 986 µl | 6.9 | 0 | 0 |
| 0 | HP | 0.5 µl | 0 | 0 | 0 |
| | HP conc. | 40 µl | 0 | 0 | 0 |
| | MG,4 ml | 13.3 µl | 0 | 0 | 0 |
| | MG, 40 ml | 28.6 µl | 0 | 0 | 0 |

TABLE 3-continued

Optimization of nucleic acid extraction.

| C. psittaci B577 genomes per ml original milk sample | DNA extraction[a] | Sample equivalent per PCR | Theoretical Chlamydia genomes per PCR | Observed Chlamydia genomes per PCR (±SEM) | Percent recovery |
|---|---|---|---|---|---|
| | MGC, 4 ml | 93.3 µl | 0 | 0 | 0 |
| | MGC, 40 ml | 986 µl | 0 | 0 | 0 |

[a]HP: HIGH PURE ® standard DNA extraction with 400 µl stabilized sample load (40 μl original specimen); HP conc HIGH PURE ® with 4 × 400 μl stabilized sample load and sample concentration by direct elution into centrifugal microconcentrator; MG, 4 ml: DNA concentration by magnetic glass particle extraction from 4 ml stabilized sample followed by standard HIGH PURE ® extraction of the eluate; MG, 40 ml: magnetic glass particle concentration and standard HIGH PURE ® extraction from 40 ml stabilized sample; MGC, 4 ml: magnetic glass particle DNA concentration from 4 ml stabilized sample followed by hybridization capture of targets to biotinylated *Chlamydia* omp1-specific oligonucleotides, streptavidin-magnetic bead extraction, and low volume elution; MGC, 40 ml: MGC extraction from 40 ml stabilized sample.

Enrichment of nucleic acids from large sample volumes of 4 or 40 ml stabilized milk was examined by using magnetic glass particles and eluting in low volume prior to standard HIGH PURE® extraction of the eluate (MG, 4 ml, MG, 40 ml; Table 3). The first part of a mRNA Isolation Kit for Blood/Bone Marrow (Roche Diagnostics Corporation) was adapted for this experiment. Data listed in Table 3 clearly indicate that this approach failed to substantially enrich for chlamydial DNA, particularly at low amounts of chlamydial targets, and that the target recovery was much lower than that of either HIGH PURE® extraction methods.

Finally, magnetic glass particle DNA concentration was combined with specific enrichment of chlamydial omp1 nucleic acid targets by hybridization capture to both 5'-biotinylated primers 191 CHOMP and CHOMP271 followed by streptavidin magnetic bead extraction and low volume elution (MGC, 4 ml, MGC, 40 ml; Table 3). For this purpose, we modified the protocol of the mRNA Isolation Kit for Blood/Bone Marrow by replacing the biotinylated Oligo $(dT)_{20}$ reagent with reagents specific for *Chlamydia* omp1. The results in Table 3 show a poor target recovery, which excluded the DNA hybridization capture method from use in high-sensitivity qPCR.

Example 6

Alternative Sample Concentration

In three independent experiments, the extraction of milk spiked with 30 *C. pneumoniae* elementary bodies per ml by microconcentrator elution with 2×200 μl $T_{10}E_{0.1}$ buffer and concentration to 40 μl was compared to direct elution with 2×20 μl. To insure complete recovery at low volume, HIGH PURE®) sample reservoirs were equilibrated at 72° C., heated buffer was transferred to the reservoirs, and the reservoirs were incubated for an additional 5 minutes before the eluate was obtained by five-minute centrifugation at 3,000×g. A total recovery of 86.8±8.8% was obtained for *C. pneumoniae* in the centrifugal ultrafiltration method, and a 90.615.7% recovery was obtained in the low volume method. Thus, the elution methods were not statistically different (p=0.71), and the low volume elution therefore was preferred because it did not require additional manipulation of the eluted DNA.

Example 7

RT-qPCR

The detection limits of *Chlamydia* omp1, 23S rRNA, 16S-23S rRNA intergenic spacer qPCRs were evaluated with or without one-step RT in a dilution series of stabilized bovine milk spiked with *C. psittaci* B577-infected mouse lung tissue (Table 4). Nucleic acids were extracted by 4-fold loading of HIGH PURE® sample reservoirs, directly eluted into centrifugal microconcentrators, and concentrated to 20-μl volume. Duplicate PCRs of triplicate samples were performed with or without one-tube reverse transcription of the assembled reactions. Reverse transcription was performed with 0.25 U SUPERSCRIPT II™ RT per qPCR for 20 min at 50° C. in the qPCR glass capillary. At 10 target copies, one-step RT improves the detection of the *Chlamydia psittaci/pecorum/pneumoniae* 23S rRNA qPCR by 2.5-fold but reduces the signal to noise ratio (FIG. 1). The results clearly indicate that the 23S rRNA target is optimal for reliable high-sensitivity detection of chlamydial genomic DNA (Table 4). The data also demonstrate substantially increased target detection with one-step reverse transcription, particularly at low target numbers, where the RT-qPCR detected approximately 10 times more 23S rRNA targets than the qPCR without RT. However, the RT-qPCR detected higher numbers of targets only in samples that were also positive in the qPCR.

TABLE 4

Detection of chlamydial DNA

| *C. psittaci* B557 genomes per ml original milk sample | Chlamydia qPCR[a] | Theoretical *Chlamydia* genomes per PCR | Observed *Chlamydia* genomes per PCR (±SEM) | Percent recovery |
|---|---|---|---|---|
| 70,000 | omp1 | 2800 | $1391^{\pm 142}$ | $49.7^{\pm 5.1}$ |
| | omp1-RT | | $1174^{\pm 83}$ | $41.9^{\pm 3.0}$ |
| | 23S rRNA | | $1147^{\pm 82}$ | $41.0^{\pm 2.9}$ |

TABLE 4-continued

Detection of chlamydial DNA

| *C. psittaci* B557 genomes per ml original milk sample | Chlamydia qPCR[a] | Theoretical *Chlamydia* genomes per PCR | Observed *Chlamydia* genomes per PCR (±SEM) | Percent recovery |
|---|---|---|---|---|
| | 23S rRNA-RT | | $4238^{\pm 502}$ | $151.4^{\pm 20.8}$ |
| | 16S-23S rRNA intergen. | | $2129^{\pm 400}$ | $76.0^{\pm 14.6}$ |
| | 16S-23S rRNA intergen.-RT | | $1476^{\pm 112}$ | $52.7^{\pm 4.0}$ |
| 7,000 | omp1 | 280 | $124^{\pm 24.3}$ | $44.2^{\pm 8.7}$ |
| | omp1-RT | | $116^{\pm 22.0}$ | $41.6^{\pm 7.9}$ |
| | 23S rRNA | | $99.4^{\pm 19.4}$ | $35.5^{\pm 6.9}$ |
| | 23S rRNA-RT | | $442^{\pm 93.0}$ | $158^{\pm 34.3}$ |
| | 16S-23S rRNA intergen. | | $183^{\pm 11.1}$ | $65.4^{\pm 4.0}$ |
| | 16S-23S rRNA intergen.-RT | | $214^{\pm 47.3}$ | $76.4^{\pm 16.9}$ |
| 700 | omp1 | 28 | $5.8^{\pm 0.7}$ | $20.7^{\pm 2.3}$ |
| | omp1-RT | | $10.4^{\pm 0.9}$ | $37.1^{\pm 3.1}$ |
| | 23S rRNA | | $9.2^{\pm 0.9}$ | $32.9^{\pm 3.3}$ |
| | 23S rRNA-RT | | $48.7^{\pm 4.5}$ | $173.8^{\pm 16.2}$ |
| | 16S-23S rRNA intergen. | | $10.9^{\pm 3.6}$ | $38.8^{\pm 12.8}$ |
| | 16S-23S rRNA intergen.-RT | | $17.0^{\pm 7.2}$ | $60.7^{\pm 25.6}$ |
| 70 | omp1 | 2.8 | $0.2^{\pm 0.1}$ | $5.8^{\pm 4.8}$ |
| | omp1-RT | | $0.6^{\pm 0.2}$ | $21.4^{\pm 8.1}$ |
| | 23S rRNA | | $0.7^{\pm 0.2}$ | $26.1^{\pm 8.2}$ |
| | 23S rRNA-RT | | $7.0^{\pm 1.8}$ | $249^{\pm 65.7}$ |
| | 16S-23S rRNA intergen. | | $0.1^{\pm 0.04}$ | $2.8^{\pm 1.6}$ |
| | 16S-23S rRNA intergen.-RT | | 0 | 0 |
| 7 | omp1 | 0.28 | 0 | 0 |
| | omp1-RT | | $0.1^{\pm 0.1}$ | $17.9^{\pm 17.9}$ |
| | 23S rRNA | | $0.3^{\pm 0.2}$ | $106^{\pm 69.3}$ |
| | 23S rRNA-RT | | $2.6^{\pm 1.7}$ | $937^{\pm 620}$ |
| | 16S-23S rRNA intergen. | | 0 | 0 |
| | 16S-23S rRNA intergen.-RT | | 0 | 0 |
| 0 | omp1 | 0 | 0 | 0 |
| | omp1-RT | 0 | 0 | 0 |
| | 23S rRNA | 0 | 0 | 0 |
| | 23S rRNA-RT | 0 | 0 | 0 |
| | 16S-23S rRNA intergen. | 0 | 0 | 0 |
| | 16S-23S rRNA intergen.-RT | 0 | 0 | 0 |

[a]RT, one-step RT-qPCR.

Example 8

Specificity of the *Chlamydia* 23 rRNA qPCR

The rRNA operon contains the genes encoding the chlamydial 16S and 23S rRNA, which are structural components of the ribosome and therefore stably present in high copy numbers in chlamydial cells. The intervening sequence between 16S-23S rRNA (16S-23S rRNA intergenic spacer) is highly transcribed but degraded rapidly. These genes are highly conserved, thus offer the potential for genus-specific detection of chlamydiae, and contain sufficient polymorphisms for differentiation among species or strains as well, in particular the 16S-23S rRNA intergenic spacer (Boman, J. et al. J. Clin. Microbiol. 1999, 37:3791-3799; Everett, K. et al. J. Syst. Bacteriol., 1997, 47:461-473; Everett, K. et al. Int. J. Syst. Bacteriol., 1999, 49:803-813; Everett, K. et al. J. Clin. Microbiol. 1999, 37:575-580).

The 23S rRNA qPCR was chosen as the standard method, and the specificity of this assay and of the various 6-FAM-labeled probes that were combined with the genus-specific set of 5'-GGGGTTGTAGGGTYGAGRAIAWRRGATC-3' (CHL23SUP; SEQ ID NO: 6); 5'-GAGAGTGGTCTC-CCCAGATTCARACTA-3' (CHL23SDN; SEQ ID NO: 7); and 5'-LCRed640-CCTGAGTAGRRCTAGACACGT-GAAAC-Phostphate-3' (CHL23LCR; SEQ ID NO: 8) primers and probes (Table 1) was evaluated. The 6-FAM probe, 5'-ACGAAARAACAARAGACKCTAWTCGAT-6-FAM-3' (CP23FLU; SEQ ID NO: 10) was designed to hybridize with *C. psittaci, C. pneumoniae,* and *C. pecorum* sequences, but not with *C. trachomatis.* Melting curves of amplification products of various chlamydial strains in the *Chlamydia psittaci/pecorum/pneumoniae* FRET qPCR were acquired (as in Example 2) by standards methods. Crude chlamydial DNAs (Kaltenboeck, B. et al. J. Clin. Microbiol 1992, 30:1098-1104) were diluted to 10,000-1,000 genome copies per 5-μl qPCR input. The melting curve analysis of the saturation amplification products of the crude DNAs of a number of chlamydial strains confirmed the specificity of the assays and probes (FIG. 2). The $T_m$ peaks for *C. psittaci* and *C. pneumoniae* strains were at approximately 55° C., while a distinct set of melting peaks for *C. pecorum* strains centered around 54° C., allowing for a limited differentiation of chlamydial species. Amplification of *C. trachomatis* and control bacteria did not yield any hybridization signal. When observed from early positivity to late saturation of the qPCR, melting peaks initially were seen at temperatures of 58.5° C. (*C. psittaci, C. pneumoniae*) or 57° C. (*C. pecorum*). These peaks shifted over the course of the qPCR to the lower saturation values. The early peaks could be recognized as right-hand shoulders in the melting curves, and the shift suggested that the lower late peaks emerged from the early ones through in vitro recombination of the amplification product.

The specificities of the *C. pneumoniae* probe 5'-AC-GAAAAAACAAAAGACGCTAATCGAT-6-FAM-3' (CPN23FLU; SEQ ID NO: 11) and the *C. trachomatis* probe 5'-ACGAAAGGAGAKMAAGACYGACCTCAAC-6-

FAM-3' (CTR23FLU; SEQ ID NO: 12) with the same set of control DNAs were also examined (data not shown). CPN23FLU exhibited weak cross-reactivity with *C. pecorum* DNA. However, the wide difference of the *C. pneumoniae* $T_m$ (63° C.) from the *C. pecorum* $T_m$ (55° C.) allows for unambiguous species discrimination. CTR23FLU hybridized only to *C. trachomatis* DNA ($T_m$: 65.4° C., LGV2; 66.3° C., MoPn; 61.5° C., S45). Collectively, these data indicated excellent specificity of the chlamydial 23S rRNA FRET qPCR, and an easy adaptation for differentiation of alleles of interest.

Alternative probes are also useful for genus- and species-specific qPCR. For example, for amplification of the *Chlamydia* 23S rRNA gene, we have developed 4 probes that allow simultaneous two-channel quantitative detection and differentiation of chlamydial targets. In this method, a carboxyfluorescein (6-FAM)-labeled *Chlamydia* 23S rRNA probe (CHL23SFLU, SEQ ID NO: 9) is combined with a BODIPYOR 630/650-labeled *C. pneumoniae-psittaci-pecorum* species-specific probe (CP23BOD; SEQ ID NO: 10) or a BODIPY® 630/650-labeled *C. pneumoniae* species-specific probe (CPN23BOD; SEQ ID NO: 11) and a Cy5.5-labeled *C. trachomatis* species-specific probe (CTR23CY5; SEQ ID NO: 12). BODIPY® 630/650 fluorescence emission detected in a 640 nm channel allows quantification of amplification and melting peak differentiation of *C. pneumoniae*, *C. psittaci*, *C. pecorum* (CP23BOD) or *C. pneumoniae* only (CPN23BOD). Cy5.5 fluorescence emission simultaneously detected in a 710 nm channel allows quantification of amplification and melting peak differentiation of *C. trachomatis* (CTR23CY5).

Example 9

Prevalence of Chlamydial Vaginal Infection in Cattle

Examination of bovine sera for antibodies against *C. psittaci* suggested a high exposure of cattle to *C. psittaci* (Kaltenboeck, B. et al. J. Clin. Microbiol 1997, 35:2293-2298). The application of nested PCR to bovine clinical specimens had further suggested such widespread infections (Kaltenboeck, B. et al. J. Clin. Microbiol 1997, 35:1835-1841). However, systematic epidemiological investigations by the nested PCR were difficult because of the laborious procedure and the requirement for highly experienced laboratory personnel. A herd of 51 clinically healthy virgin Holstein heifers were sampled four times at weekly intervals. Vaginal cytobrush specimens (HISTOBRUSH™; Fisher Scientific, Suwanee, Ga.) were obtained by 10 sec of rotation in the vaginal vestibulum, brushes were immediately transferred to 400 μl RNA/DNA Stabilization Reagent in a 1.5 ml screw-cap microcentrifuge tube, mixed, and the brush handles were cut off. After five minutes of centrifugation at 3,000×g and room temperature, the brushes were removed; nucleic acids were extracted by use of the HIGH PURE® kit, and eluted 2× at 72° C. in 20 μl $T_{10}E_{0.1}$ buffer. Duplicate *Chlamydia* 23S rRNA qPCRs were performed with genus-specific primers/probes CHL23SUP, CHL23SDN and CHL23LCR, and the *C. psittaci/pecorum/pneumoniae*-specific probe CP23FLU. The strain identification of positive specimens was confirmed by *C. psittaci* B577- and *C. pecorum*-specific omp1 qPCRs.

A surprisingly high prevalence of *Chlamydia* vaginal infection was found, with 51% (26 cows) of virgin heifers positive at least once during the 4-week examination period. Surprisingly, about 2/3 (19 cows) of the positive animals harbored *C. pecorum*, and only 1/3 (9 cows) had *C. psittaci* infection. Two heifers were positive for both chlamydial species in different samples, and six were positive more than once for *C. pecorum*. Interestingly, the number of chlamydiae detected per specimen was very low, 0.71 genomes per qPCR, indicating that low-level chlamydial infections have symptoms that lie below the detection level of clinical examination.

Example 10

Recovery of DNA after Mechanical Disruption

Using detection of the *Chlamydia* 23S rRNA gene as a case study, we tested if A) very low amounts of nucleic acids could be retrieved and detected in the presence of zirconia/silica beads during sample collection and nucleic acid extraction; and B) if the beads retained nucleic acids that could be retrieved during the final nucleic acid elution step.

A. Twenty-eight *C. pneumoniae* elementary bodies per ml were added to fresh bovine milk such that a theoretical maximum of 2.5 *C. pneumoniae* genomes were present per 5 μl extracted nucleic acid solution used as input in a 20 μl *Chlamydia* 23S rRNA FRET-qPCR. Eight 700 μl milk samples were each mixed with 700 μl HIGH PURE®) Binding Buffer. To four of these samples 0.3 g silica-zirconia beads of 0.1 mm diameter were added. Proteinase K solution was added, and the samples were horizontally incubated at 72° C. for 30 min with continuous shaking at 1200 rpm. Subsequently, the complete contents including the silica-zirconia beads of these samples were transferred to the HIGH PURE® sample reservoir. Nucleic acids from both sets of samples were extracted according to the standard procedure described herein. Three qPCRs were performed for each sample. The results are shown in Table 5.

TABLE 5

DNA detection in the presence or absence of zirconia/silica beads

| | Theoretical *C. pneumoniae* genomes/qPCR | *C. pneumoniae* genomes determined/qPCR | Percent recovery | p for difference |
|---|---|---|---|---|
| No beads | 2.5 | 2.04 ± 1.42 | 81.6 ± 56.80 | 0.70 |
| Beads | 2.5 | 1.84 ± 1.00 | 73.6 ± 40.00 | 0.70 |

The data in Table 5 indicate that there is no significant difference in recovery of *C. pneumoniae* DNA in the presence or absence of zirconia/silica beads. Therefore these beads are suitable for use in the mechanical disruption of membranes of microorganisms for high sensitivity nucleic acid detection methods.

B. Seventeen *C. pneumoniae* elementary bodies per ml were added to fresh bovine milk such that a theoretical maximum of 1.5 *C. pneumoniae* genomes were present per 5 μl extracted nucleic acid solution used as input in a 20 μl *Chlamydia* 23S rRNA FRET-qPCR. Twelve 700 μl milk samples were each mixed with 700 μl HIGH PURE® Binding Buffer to which 0.3 g zirconia/silica beads of 0.1 mm diameter had been added. Proteinase K solution was added, and the samples were horizontally incubated at 72° C. for 30 min with continuous shaking at 1200 rpm. Subsequently, the complete contents including the zirconia/silica beads of six of these samples were transferred to the HIGH PURE(g) sample reservoir. From the remaining six samples, the supernatant solutions, but not the sediments of zirconia/silica beads, were transferred to HIGH PURE® sample reservoirs. Nucleic acids from both sets of samples were extracted according to the standard procedure described herein. Four qPCRs were performed for each sample. The results are shown in Table 6.

TABLE 6

Extraction of DNA from zirconia/silica beads

| | Theoretical C. pneumoniae genomes/qPCR | C. pneumoniae genomes determined/qPCR | Percent recovery | p for difference |
|---|---|---|---|---|
| Supernatant only | 1.5 | 0.75 ± 0.63 | 50.00 ± 42.00 | 0.028 |
| Supernatant and beads | 1.5 | 1.20 ± 0.76 | 80.00 ± 50.67 | 0.028 |

The data in Table 6 indicate that the recovery of *C. pneumoniae* DNA in the presence of zirconia/silica beads was significantly higher when the beads were included in the elution buffer than when the beads were excluded. For high sensitivity nucleic acid detection methods it is therefore desirable to extract DNA from the beads and the sample supernatant.

Other Embodiments

Modifications and variations of the described methods of the invention will be apparent to those skilled in the art without departing from the scope and spirit of the invention. Although the invention has been described in connection with specific desirable embodiments, it should be understood that the invention as claimed should not be unduly limited to such specific embodiments. Indeed, various modifications of the described modes for carrying out the invention, which are obvious to those skilled in the art, are intended to be within the scope of the invention.

All publications, patents, and patent applications mentioned in this specification are hereby incorporated by reference to the same extent as if each individual publication, patent, or patent application was specifically and individually to be incorporated by reference.

Other embodiments are within the claims.

What is claimed is:

1. A method of determining an amount of a target nucleic acid in a sample, said method comprising the steps of:

a) providing said sample;

b) contacting an aliquot of said sample with a solid support, wherein nucleic acid in said aliquot binds to said solid support;

c) eluting said nucleic acid bound to said solid support with at least two sequential volumes of 5-25 μl to produce a concentrated nucleic acid sample;

d) contacting said concentrated nucleic acid sample of step (c) with oligonucleotide primers capable of amplifying said target nucleic acid under appropriate conditions, a first probe labeled with a donor fluorophore, and a second probe labeled with an acceptor fluorophore to produce an amplification sample, wherein said first and second probes hybridize proximally to one another on said target nucleic acid, and wherein energy transferred from said donor fluorophore induces fluorescence from said acceptor fluorophore; and e) performing an amplification on said amplification sample to produce an amplification product, wherein said amplification comprises a series of step-down cycles followed by a series of fluorescence acquisition cycles, wherein each of said fluorescence acquisition cycles comprises detection of fluorescence from said acceptor fluorophore, wherein the kinetics of an increase in intensity of fluorescence from said acceptor fluorophore are indicative of the amount of said target nucleic acid in said sample.

2. A method of determining an amount of a target nucleic acid in a sample, said method comprising the steps of:

a) providing said sample;

b) contacting an aliquot of said sample with a solid support, wherein nucleic acid in said aliquot binds to said solid support;

c) eluting said nucleic acid bound to said solid support in step (b) to produce a volume of eluate and reducing said volume by centrifugal ultrafiltration to produce a concentrated nucleic acid sample;

d) contacting said concentrated nucleic acid sample of step (c) with oligonucleotide primers capable of amplifying said target nucleic acid under appropriate conditions, a first probe labeled with a donor fluorophore, and a second probe labeled with an acceptor fluorophore to produce an amplification sample, wherein said first and second probes hybridize proximally to one another on said target nucleic acid, and wherein energy transferred from said donor fluorophore induces fluorescence from said acceptor fluorophore; and e) performing an amplification on said amplification sample to produce an amplification product, wherein said amplification comprises a series of step-down cycles followed by a series of fluorescence acquisition cycles, wherein each of said fluorescence acquisition cycles comprises detection of fluorescence from said acceptor fluorophore, wherein the kinetics of an increase intensity of fluorescence from said acceptor fluorophore are indicative of the amount of said target nucleic acid in said sample.

3. A method of determining an amount of a target nucleic acid in a sample, said method comprising the steps of:

a) providing a sample;

b) contacting a plurality of aliquots of said sample with a plurality of solid supports, wherein nucleic acid in said plurality of aliquots binds to said plurality of solid supports;

c) eluting said nucleic acid bound to each of said plurality of solid supports in step (b) to produce a plurality of volumes of eluate;

d) combining said volumes of (c) to produce a combined volume;

e) reducing said combined volume by centrifugal ultrafiltration to produce a concentrated nucleic acid sample;

f) contacting said concentrated nucleic acid sample of step (e) with oligonucleotide primers capable of amplifying said target nucleic acid under appropriate conditions, a first probe labeled with a donor fluorophore, and a second probe labeled with an acceptor fluorophore to produce an amplification sample, wherein said first and second probes hybridize proximally to one another on said target nucleic acid, and wherein energy transferred from said donor fluorophore induces fluorescence from said acceptor fluorophore; and g) performing an amplification on said amplification sample to produce an amplification product, wherein said amplification comprises a series of step-down cycles followed by a series of fluorescence acquisition cycles, wherein each of said fluorescence acquisition cycles comprises detection of fluorescence from said acceptor fluorophore, wherein the kinetics of an increase in intensity of fluorescence from said acceptor fluorophore are indicative of the amount of said target nucleic acid in said sample.

4. A method of diagnosing a microbial infection in a mammal, said method comprising the steps of:
  a) providing a sample of a biological material from said mammal;
  b) preparing said sample for nucleic acid extraction to produce a nucleic acid sample;
  c) contacting an aliquot of said nucleic acid sample with a solid support, wherein nucleic acid in said aliquot binds to said solid support;
  d) eluting said nucleic acid from said solid support with at least two sequential volumes of 5-25 µl to produce a concentrated nucleic acid sample;
  e) contacting said concentrated nucleic acid sample of step (d) with oligonucleotide primers capable of amplifying a target nucleic acid under appropriate conditions, a first probe labeled with a donor fluorophore, and a second probe labeled with an acceptor fluorophore to produce an amplification sample, wherein said first and second probes hybridize proximally to one another on said target nucleic acid, and wherein energy transferred from said donor fluorophore induces fluorescence from said acceptor fluorophore; and
  f) performing an amplification on said amplification sample to produce an amplification product, wherein said amplification comprises a series of step-down cycles followed by a series of fluorescence acquisition cycles, wherein each of said fluorescence acquisition cycles comprises detection of fluorescence from said acceptor fluorophore, wherein fluorescence from said acceptor fluorophore is indicative of a presence of said microbial infection, and an absence of fluorescence from said acceptor fluorophore is indicative of an absence of said microbial infection.

5. A method of diagnosing a microbial infection in a mammal, said method comprising the steps of:
  a) providing a sample of a biological material from said mammal;
  b) preparing said sample for nucleic acid extraction to produce a nucleic acid sample;
  c) contacting an aliquot of said nucleic acid sample with a solid support, wherein nucleic acid in said aliquot binds to said solid support;
  d) eluting said nucleic acid bound to said solid support in step (c) to produce a volume of eluate and reducing said volume by centrifugal ultrafiltration to produce a concentrated nucleic acid sample;
  e) contacting said concentrated nucleic acid sample of step (d) with oligonucleotide primers capable of amplifying a target nucleic acid under appropriate conditions, a first probe labeled with a donor fluorophore, and a second probe labeled with an acceptor fluorophore to produce an amplification sample, wherein said first and second probes hybridize proximally to one another on said target nucleic acid, and wherein energy transferred from said donor fluorophore induces fluorescence from said acceptor fluorophore; and
  f) performing an amplification on said amplification sample to produce an amplification product, wherein said amplification comprises a series of step-down cycles followed by a series of fluorescence acquisition cycles, wherein each of said fluorescence acquisition cycles comprises detection of fluorescence from said acceptor fluorophore, wherein fluorescence from said acceptor fluorophore is indicative of a presence of said microbial infection, and an absence of fluorescence from said acceptor fluorophore is indicative of an absence of said microbial infection.

6. A method of diagnosing a microbial infection in a mammal, said method comprising the steps of:
  a) providing a sample of a biological material from said mammal;
  b) preparing said sample for nucleic acid extraction to produce a nucleic acid sample;
  c) contacting a plurality of aliquots of said sample with a plurality of solid supports, wherein nucleic acid in said plurality of aliquots binds to said plurality of solid supports;
  d) eluting said nucleic acid bound to each of said plurality of solid supports in step (c) to produce a plurality of volumes of eluate;
  e) combining said volumes of (d) to produce a combined volume;
  f) reducing said combined volume by centrifugal ultrafiltration to produce a concentrated nucleic acid sample;
  g) contacting said concentrated nucleic acid sample of step (f) with oligonucleotide primers capable of amplifying a target nucleic acid under appropriate conditions, a first probe labeled with a donor fluorophore, and a second probe labeled with an acceptor fluorophore to produce an amplification sample, wherein said first and second probes hybridize proximally to one another on said target nucleic acid, and wherein energy transferred from said donor fluorophore induces fluorescence from said acceptor fluorophore; and
  h) performing an amplification on said amplification sample to produce an amplification product, wherein said amplification comprises a series of step-down cycles followed by a series of fluorescence acquisition cycles, wherein each of said fluorescence acquisition cycles comprises detection of fluorescence from said acceptor fluorophore, wherein fluorescence from said acceptor fluorophore is indicative of a presence of said microbial infection, and an absence of fluorescence from said acceptor fluorophore is indicative of an absence of said microbial infection.

7. The method of any of claims 1-6, wherein said solid support comprises glass fiber fleece.

8. The method of any of claims 1-6, wherein said series of step-down cycles comprises six cycles having a first annealing temperature of the melting temperature of said primers, nine cycles having a second annealing temperature of 2° C. lower than said first annealing temperature, and three cycles having a third annealing temperature of 4° C. lower than said first annealing temperature.

9. The method of any of claims 1-6, wherein said series of fluorescence acquisition cycles comprises six or more cycles having an annealing temperature lower than the melting temperature of said probes, wherein in each cycle, fluorescence detection of said acceptor fluorophore occurs under conditions in which said first and second probes hybridize to said target nucleic acid.

10. The method of any of claims 1-6, wherein said donor fluorophore comprises fluorescein or carboxyfluorescein and said acceptor fluorophore comprises 6-(((4,4-difluoro-5-(2-thienyl)-4-bora-3a,4a-diaza-s-indacene-3-yl)styryloxy) acetyl)aminohexanoic acid, or Cy5.5.

11. The method of any of claims 1-6, further comprising the step of contacting said concentrated nucleic acid sample with reverse transcriptase under conditions appropriate to reverse transcribe any RNA in said concentrated nucleic acid sample before said amplification.

12. The method of claim 11, wherein said reverse transcriptase is stable at $\leq 65°$ C.

13. The method of claim 11, wherein prior to reverse transcription, said nucleic acid sample is incubated at between 65° C. and 80° C.

14. The method of any claims 1-6, wherein said target nucleic acid is present in a single genome in two or more copies.

15. The method of any of claims 1-6, wherein said target nucleic acid is DNA from *Chlamydia*.

16. The method of claim 15, wherein said DNA from *Chlamydia comprises a* 23S rRNA gene.

17. The method of any of claims 1-6, wherein said primers are genus-specific.

18. The method of any of claims 1-6, wherein one of said first or second probes is genus-specific and the other of said probes is species- or strain-specific.

19. The method of any of claims 1-6, wherein said amplification occurs in a glass capillary.

20. The method of claim 4, 5, or 6, wherein said mammal is a human.

* * * * *

SEQUENCE LISTING

```
<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<221> NAME/KEY: misc_feature
<222> LOCATION: 3, 6, 18, 24
<223> OTHER INFORMATION: n = Inosine
<220> FEATURE:
<223> OTHER INFORMATION: based on Chlamydia

<400> SEQUENCE: 1
gcnytntggg artgyggntg ygcnac                                26

<210> SEQ ID NO 2
<211> LENGTH: 29
<212> TYPE: DNA
<213> ORGANISM: Artificial Sequence
<220> FEATURE:
<221> NAME/KEY: misc_feature
<222> LOCATION: 6, 12, 18, 27
<223> OTHER INFORMATION: n = Inosine
<220> FEATURE:
<223> OTHER INFORMATION: based on Chlamydia

<400> SEQUENCE: 2
gctckngacc antkwacncc aatgtangg                             29

<210> SEQ ID NO 3
<211> LENGTH: 29
<212> TYPE: DNA
<213> ORGANISM: Artificial Sequence
<220> FEATURE:
<221> NAME/KEY: misc_feature
<222> LOCATION: 6, 18, 24
<223> OTHER INFORMATION: n = Inosine
```

-continued

<220> FEATURE:
<223> OTHER INFORMATION: based on Chlamydia

<400> SEQUENCE: 3
gaytgngcrt attggaankm wgcnccyaa 29

<210> SEQ ID NO 4
<211> LENGTH: 27
<212> TYPE: DNA
<213> ORGANISM: Artificial Sequence
<220> FEATURE:
<223> OTHER INFORMATION: based on Chlamydia psittaci

<400> SEQUENCE: 4
tacattcaac atttcaattt taggatt 27

<210> SEQ ID NO 5
<211> LENGTH: 27
<212> TYPE: DNA
<213> ORGANISM: Artificial Sequence
<220> FEATURE:
<223> OTHER INFORMATION: based on Chlamydia pecorum

<400> SEQUENCE: 5
aacgttkart tcttgaacgc gaggttt 27

<210> SEQ ID NO 6
<211> LENGTH: 28
<212> TYPE: DNA
<213> ORGANISM: Artificial Sequence
<220> FEATURE:
<221> NAME/KEY: misc_feature
<222> LOCATION: 20
<223> OTHER INFORMATION: n = Inosine
<220> FEATURE:
<223> OTHER INFORMATION: based on Chlamydia

<400> SEQUENCE: 6
ggggttgtag ggtygagran awrrgatc 28

<210> SEQ ID NO 7
<211> LENGTH: 27
<212> TYPE: DNA
<213> ORGANISM: Artificial Sequence
<220> FEATURE:
<223> OTHER INFORMATION: based on Chlamydia

<400> SEQUENCE: 7
gagagtggtc tccccagatt caracta 27

<210> SEQ ID NO 8
<211> LENGTH: 26
<212> TYPE: DNA
<213> ORGANISM: Artificial Sequence
<220> FEATURE:
<223> OTHER INFORMATION: based on Chlamydia

<400> SEQUENCE: 8
cctgagtagr rctagacacg tgaaac 26

<210> SEQ ID NO 9
<211> LENGTH: 26
<212> TYPE: DNA
<213> ORGANISM: Artificial Sequence
<220> FEATURE:
<223> OTHER INFORMATION: based on Chlamydia

<400> SEQUENCE: 9
graygahaca gggtgatagt cccgta    26

<210> SEQ ID NO 10
<211> LENGTH: 27
<212> TYPE: DNA
<213> ORGANISM: Artificial Sequence
<220> FEATURE:
<223> OTHER INFORMATION: based on Chlamydia pecorum, Chlamydia psittaci,
      and Chlamydia pneumoniae

<400> SEQUENCE: 10
acgaaaraac aaragackct awtcgat 27

<210> SEQ ID NO 11
<211> LENGTH: 27
<212> TYPE: DNA
<213> ORGANISM: Artificial Sequence
<220> FEATURE:
<223> OTHER INFORMATION: based on Chlamydia pneumoniae

<400> SEQUENCE: 11
acgaaaaaac aaaagacgct aatcgat 27

<210> SEQ ID NO 12
<211> LENGTH: 28
<212> TYPE: DNA
<213> ORGANISM: Artificial Sequence
<220> FEATURE:
<223> OTHER INFORMATION: based on Chlamydia trachomatis

<400> SEQUENCE: 12
acgaaaggag akmaagacyg acctcaac 28

<210> SEQ ID NO 13
<211> LENGTH: 22
<212> TYPE: DNA
<213> ORGANISM: Artificial Sequence
<220> FEATURE:
<223> OTHER INFORMATION: based on Chlamydia

<400> SEQUENCE: 13
tgactaggtt grgcaagyrt yt 22

<210> SEQ ID NO 14
<211> LENGTH: 32
<212> TYPE: DNA
<213> ORGANISM: Artificial Sequence
<220> FEATURE:
<221> NAME/KEY: misc_feature
<222> LOCATION: 8
<223> OTHER INFORMATION: n = Inosine
<220> FEATURE:
<223> OTHER INFORMATION: based on Chlamydia

<400> SEQUENCE: 14
aaagacanat aytcttaaac gtctattatt at 32

<210> SEQ ID NO 15
<211> LENGTH: 25
<212> TYPE: DNA
<213> ORGANISM: Artificial Sequence
<220> FEATURE:
<221> NAME/KEY: misc_feature
<222> LOCATION: 9
<223> OTHER INFORMATION: n = Inosine
<220> FEATURE:

-continued

```
<223> OTHER INFORMATION: based on Chlamydia

<400> SEQUENCE: 15
cttaacaanr caaawgaaat agaat                                              25

<210> SEQ ID NO 16
<211> LENGTH: 25
<212> TYPE: DNA
<213> ORGANISM: Artificial Sequence
<220> FEATURE:
<223> OTHER INFORMATION: based on Chlamydia psittaci

<400> SEQUENCE: 16
cgtaaactaa atgttttgga aacaa                                              25
```